(12) United States Patent
Knight et al.

(10) Patent No.: US 9,346,068 B2
(45) Date of Patent: *May 24, 2016

(54) DISPENSERS

(71) Applicant: Rieke Corporation, Auburn, IN (US)

(72) Inventors: Simon Christopher Knight, Brigend (GB); Joseph Stanley Brunton, Fordham (GB); David John Pritchett, Ashby de la Zouch (GB)

(73) Assignee: Rieke Corporation, Auburn, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,040

(22) Filed: Dec. 12, 2014

(65) Prior Publication Data

US 2015/0100017 A1 Apr. 9, 2015

Related U.S. Application Data

(63) Continuation of application No. 14/318,981, filed on Jun. 30, 2014, now Pat. No. 8,939,323, which is a continuation of application No. PCT/IB2013/050101, filed on Jan. 4, 2013.

(30) Foreign Application Priority Data

Jan. 4, 2012 (GB) .................................. 1200258.0

(51) Int. Cl.
*B67B 1/00* (2006.01)
*B05B 11/00* (2006.01)
(Continued)

(52) U.S. Cl.
CPC ........... *B05B 11/0027* (2013.01); *A61J 7/0053* (2013.01); *A61M 11/00* (2013.01);
(Continued)

(58) Field of Classification Search
CPC ............ B05B 11/0027; B05B 11/0005; B05B 11/0072; B05B 11/0075; B05B 11/3001; B05B 11/3015; B05B 11/3074; B05B 11/0048; B05B 11/3047; B05B 11/3069; A61J 7/0053; A61M 11/00; A61M 31/00; A61M 2205/276
USPC ............ 222/153.13, 567, 153.12, 322, 402.1, 222/402.11, 402.13, 402.14, 402.25, 256, 222/259, 321.7, 321.9, 387, 321.3, 153.1, 222/501; 141/22, 322, 379; 239/333; 220/246, 245, 281, 321, 323, 835, 315
See application file for complete search history.

(56) References Cited

U.S. PATENT DOCUMENTS 1,283,050 A * 10/1918 Berg ..................... B65D 35/40
222/207

(Continued)

FOREIGN PATENT DOCUMENTS

DE 39 29 064 A 1/1991
EP 0 098 939 A2 1/1984
(Continued)

OTHER PUBLICATIONS

European Patent Application 04255318 Search Report mailed Jun. 14, 2006.
European Patent Application 05256914.2 Extended Search Report mailed Mar. 2, 2006.
(Continued)

*Primary Examiner* — J. Casimer Jacyna
*Assistant Examiner* — Benjamin R Shaw
(74) *Attorney, Agent, or Firm* — Woodard Emhardt Moriarty McNett & Henry LLP

(57) ABSTRACT

The invention relates to dispensers for fluid products, particularly oral dosing of medicines. The dispenser is a pump dispenser and has a separate nozzle attachment. The nozzle and dispenser may be uncoupled in a holding position or coupled position. A child resistance feature is disclosed which prevents unauthorized coupling of the dispenser and nozzle, thereby preventing unauthorized dispensing of product. The child resistance feature only allows coupling of the dispenser and nozzle when a coupling control element is triggered and then maintains this coupling with additional features. A protective cover for the dispenser is also disclosed, which covers the nozzle attachment and pump plunger button.

35 Claims, 14 Drawing Sheets

(51) Int. Cl.
*A61M 11/00* (2006.01)
*A61J 7/00* (2006.01)
*A61M 31/00* (2006.01)

(52) U.S. Cl.
CPC ............ *A61M 31/00* (2013.01); *B05B 11/0005* (2013.01); *B05B 11/0072* (2013.01); *B05B 11/0075* (2013.01); *B05B 11/3001* (2013.01); *B05B 11/3005* (2013.01); *B05B 11/3015* (2013.01); *B05B 11/3074* (2013.01); *A61M 2205/276* (2013.01); *B05B 11/0048* (2013.01); *B05B 11/3047* (2013.01); *B05B 11/3069* (2013.01)

(56) References Cited

U.S. PATENT DOCUMENTS

| | | | |
|---|---|---|---|
| 2,469,746 A * | 5/1949 | Sanchis | B67D 3/02 141/296 |
| 2,774,517 A | 12/1956 | Teegardin et al. | |
| 2,919,056 A | 12/1959 | Collins | |
| 3,379,136 A | 4/1968 | Corsette | |
| 4,118,152 A | 10/1978 | Bron | |
| 4,277,001 A | 7/1981 | Nozawa | |
| 4,286,736 A | 9/1981 | Corsette et al. | |
| 4,343,417 A | 8/1982 | Corsette | |
| 4,360,130 A | 11/1982 | Nishimura et al. | |
| 4,364,718 A | 12/1982 | Beun et al. | |
| 4,371,098 A | 2/1983 | Nozawa et al. | |
| 4,376,495 A * | 3/1983 | Spatz | B65D 35/40 222/207 |
| 4,496,082 A | 1/1985 | Corsette | |
| 4,511,065 A | 4/1985 | Corsette | |
| 4,515,298 A | 5/1985 | Czech | |
| 4,589,573 A | 5/1986 | Tada | |
| 4,673,109 A | 6/1987 | Cassia | |
| 4,771,925 A | 9/1988 | Stoffler et al. | |
| 4,775,079 A | 10/1988 | Grothoff | |
| 4,776,498 A | 10/1988 | Maerte et al. | |
| 4,790,442 A * | 12/1988 | Gach | B65D 47/0885 215/216 |
| 4,811,871 A | 3/1989 | Wass et al. | |
| 4,856,679 A | 8/1989 | Czech | |
| 4,872,596 A * | 10/1989 | Corsette | B05B 11/0048 137/512.4 |
| 4,890,773 A | 1/1990 | Corsette | |
| 4,958,752 A | 9/1990 | Maerte et al. | |
| 5,016,780 A | 5/1991 | Moretti | |
| 5,096,094 A | 3/1992 | Guilbert | |
| 5,115,980 A | 5/1992 | SKorka | |
| 5,165,577 A | 11/1992 | Ophardt | |
| 5,282,552 A | 2/1994 | Ophardt | |
| 5,353,969 A | 10/1994 | Balderrama | |
| 5,373,970 A | 12/1994 | Ophardt | |
| 5,401,148 A | 3/1995 | Foster et al. | |
| 5,431,309 A | 7/1995 | Ophardt | |
| 5,445,288 A | 8/1995 | Banks | |
| 5,462,204 A * | 10/1995 | Finn | B05B 1/3066 222/137 |
| 5,489,044 A | 2/1996 | Ophardt | |
| 5,548,943 A | 8/1996 | Behar et al. | |
| 5,676,277 A | 10/1997 | Ophardt | |
| 5,738,250 A | 4/1998 | Gillingham et al. | |
| 5,813,576 A | 9/1998 | Iizuka et al. | |
| 5,878,916 A | 3/1999 | DeJonge | |
| 5,878,922 A | 3/1999 | Boring | |
| 5,904,272 A | 5/1999 | Kaufman et al. | |
| 5,975,360 A | 11/1999 | Ophardt | |
| 5,988,456 A * | 11/1999 | Laible | B67D 7/0294 222/464.1 |
| 6,045,008 A | 4/2000 | Gonzalez et al. | |
| 6,053,368 A | 4/2000 | Geimer | |
| 6,062,433 A | 5/2000 | Fuchs | |
| 6,082,586 A | 7/2000 | Banks | |
| 6,126,042 A | 10/2000 | Meshberg | |
| 6,179,164 B1 | 1/2001 | Fuchs | |
| 6,240,979 B1 | 6/2001 | Lorscheidt | |
| 6,257,454 B1 | 7/2001 | Ritsche | |
| 6,343,724 B1 | 2/2002 | Ophardt et al. | |
| 6,409,050 B1 | 6/2002 | Ophardt et al. | |
| 6,516,976 B2 | 2/2003 | Lewis et al. | |
| 6,533,145 B2 | 3/2003 | Lewis et al. | |
| 6,540,117 B2 | 4/2003 | Powling | |
| 6,540,157 B2 | 4/2003 | Ophardt | |
| 6,543,651 B2 | 4/2003 | Lewis et al. | |
| 6,557,736 B1 | 5/2003 | Ophardt | |
| 6,575,334 B2 | 6/2003 | Lewis et al. | |
| 6,575,335 B2 | 6/2003 | Lewis et al. | |
| 6,601,736 B2 | 8/2003 | Ophardt et al. | |
| 7,004,356 B1 | 2/2006 | Sayers | |
| 7,011,237 B1 | 3/2006 | Sayers et al. | |
| 7,044,339 B1 * | 5/2006 | Kuo | B05B 11/3059 222/182 |
| 7,104,426 B2 | 9/2006 | Suzuki | |
| 7,325,704 B2 | 2/2008 | Kasting | |
| 7,367,476 B2 | 5/2008 | Law et al. | |
| 7,461,762 B2 | 12/2008 | Law et al. | |
| 7,654,418 B2 | 2/2010 | Law et al. | |
| 7,690,535 B2 | 4/2010 | Law et al. | |
| 7,798,348 B2 * | 9/2010 | Sawyer | B65D 47/0809 215/237 |
| 7,891,522 B2 | 2/2011 | Law et al. | |
| 8,118,193 B2 | 2/2012 | Law | |
| 8,556,130 B2 | 10/2013 | Law et al. | |
| 2002/0027144 A1 | 3/2002 | Lacout | |
| 2002/0148860 A1 * | 10/2002 | Cohen | B05B 11/0059 222/321.7 |
| 2003/0132252 A1 | 7/2003 | Rossignol | |
| 2003/0201286 A1 | 10/2003 | Ophardt | |
| 2004/0129733 A1 | 7/2004 | Schultz | |
| 2004/0217137 A1 | 11/2004 | Ophardt | |
| 2005/0035153 A1 * | 2/2005 | Brown | B01F 5/0682 222/145.6 |
| 2005/0051579 A1 | 3/2005 | Kasting | |
| 2005/0133475 A1 * | 6/2005 | Goto | B65D 47/0814 215/237 |
| 2005/0205607 A1 * | 9/2005 | Hierzer | B65D 47/0804 222/153.1 |
| 2006/0043117 A1 | 3/2006 | Law et al. | |
| 2007/0200010 A1 | 8/2007 | Girerd | |
| 2007/0215643 A1 | 9/2007 | Law et al. | |
| 2008/0083782 A1 * | 4/2008 | Heusser | A61C 5/064 222/145.5 |
| 2008/0197149 A1 | 8/2008 | Law et al. | |
| 2008/0308183 A1 | 12/2008 | Law | |
| 2009/0065531 A1 | 3/2009 | Decottignies | |
| 2009/0212074 A1 | 8/2009 | Brouwer | |
| 2009/0218008 A1 * | 9/2009 | Law | A45D 34/04 141/311 R |
| 2010/0209870 A1 * | 8/2010 | Thomas | A61C 17/0202 433/89 |
| 2010/0276515 A1 | 11/2010 | Milanese | |
| 2012/0097714 A1 | 4/2012 | Hoefte et al. | |
| 2012/0261418 A1 * | 10/2012 | Cronin | B65D 50/046 220/277 |
| 2013/0008924 A1 | 1/2013 | Lafosse | |
| 2013/0200106 A1 * | 8/2013 | Kang | B65D 55/02 222/153.13 |
| 2014/0312072 A1 | 10/2014 | Knight et al. | |

FOREIGN PATENT DOCUMENTS

| | | |
|---|---|---|
| EP | 0 274 256 A1 | 7/1988 |
| EP | 0 327 421 A1 | 8/1989 |
| EP | 0 389 688 A2 | 10/1990 |
| EP | 0 509 863 A1 | 10/1992 |
| EP | 0 600 286 A2 | 6/1994 |
| EP | 0 703 831 B1 | 12/1998 |
| EP | 1 092 447 A2 | 4/2001 |
| EP | 1 190 775 A1 | 3/2002 |
| EP | 1 015 341 B1 | 1/2004 |
| EP | 1 449 595 A1 | 8/2004 |

(56) References Cited

FOREIGN PATENT DOCUMENTS

| EP | 1 514 607 A2 | 3/2005 |
|---|---|---|
| EP | 1 629 900 A2 | 3/2006 |
| EP | 1 671 705 A1 | 6/2006 |
| EP | 1 676 640 A1 | 7/2006 |
| EP | 2 095 882 A1 | 9/2009 |
| EP | 2 133 153 A1 | 12/2009 |
| EP | 2 153 908 A1 | 2/2010 |
| EP | 2 353 727 | 8/2011 |
| GB | 1149805 | 4/1969 |
| GB | 2360273 A | 9/2001 |
| GB | 2360273 A | 9/2001 |
| JP | H08-011921 A | 1/1996 |
| WO | WO 99/49769 A1 | 10/1999 |
| WO | WO 03/101620 A1 | 12/2003 |
| WO | WO 2005/049477 A2 | 6/2005 |
| WO | WO 2010/023462 A1 | 4/2010 |
| WO | WO 2012/001375 A1 | 1/2012 |

OTHER PUBLICATIONS

European Search Report in corresponding EP 11250032.7 dated May 20, 2011.
Hygiene-Technik Inc., A member of the Ophardt Group of Companies, UX10 Lotion or Foam Soap Dispenser, 2004, pp. 2.
PCT/GB2011/001001 Search Report and Written Opinion dated Nov. 24, 2011.
PCT/GB2011/001002 Search Report and Written Opinion dated Sep. 26, 2011.
PCT/IB2013/050101 International Preliminary Report on Patentability dated Jul. 8, 2014.
Pictures of Umbrella Valve from RD Industries of Omaha, Nebraska (Pictures 1-6), Jan. 4, 2005.
United Kingdom Patent Application 1100129.4 Search Report mailed Mar. 23, 2011.
U.S. Appl. No. 12/685,064 to David John Pritchett, Office Action mailed Aug. 17, 2012.

* cited by examiner

DISPENSERS

CROSS-REFERENCE TO RELATED APPLICATION

This application is a continuation of U.S. patent application Ser. No. 14/318,981 filed Jun. 30, 2014, which is a continuation of International Application No. PCT/IB2013/050101, filed Jan. 4, 2013, which claims the benefit of United Kingdom Application No. GB1200258.0, filed Jan. 4, 2012, the entire disclosures of which are hereby incorporated by reference.

This invention has to do with dispensers for fluid products. The ideas described here have particular application in dispensers or oral dosing devices to be used for oral dosing of medicines, especially to children, but they can have other uses.

This application develops proposals put forward in our PCT/GB2011/001002, published as WO2012/001375 after the priority date of the present application, and referred to herein as the "earlier application". The entire contents of the earlier application are incorporated herein by reference as if repeated herein, for all purposes.

BACKGROUND

Conventionally, liquid oral medicines are administered with small spoons typically holding 5 ml. The medicine is poured from a bottle into the spoon. Where smaller doses are needed, e.g. for children, the spoon may be part-filled, or a smaller spoon used. It is not easy to pour a small dose accurately from a bottle. An alternative method is dosing by squirting into the mouth from a syringe. It is then easy to charge the accurate amount, but syringes are difficult to fill unless the container is specially adapted, and much more difficult than spoons to clean and dry.

Special problems arise when dosing very young children and babies, who may be unable to swallow all the intended dose at once. It is no use dispensing a dose accurately if the child chokes or spits part of it out.

It may be considered to use a pump dispenser in which, by a predetermined stroke of a piston-cylinder pump chamber mounted on a product container, a uniform volume can be dosed from the container to an outlet nozzle. Such dispensers are known for dosing animals. If a child could be dosed directly from the nozzle, a convenient way of providing fast, predetermined doses without a separate spoon would be available.

However pump dispensers in general have drawbacks in respect of this use. Fluid residues remain in the outlet nozzle after each stroke. These may dry out or become contaminated. In practice, pump outlet nozzles cannot be adequately hygienic even if a cover cap is provided. Moreover pump mechanisms are valved for forward flow. If a child sucked on the nozzle they might receive an excessive dose.

Here we put forward new ideas for dispensers which address various issues discussed above.

SUMMARY

The Invention

Our proposals relate in general to a dispenser for fluid products, preferably a pump dispenser, having a discharge outlet with an outlet opening. The dispenser is operable to dispense a fluid product from a supply container in doses from the discharge outlet. In a pump dispenser, the typical dosing action is reciprocation of a pump plunger, which alters the volume of a pump chamber connected via an inlet to the supply container and via a discharge channel to the outlet opening. Usually the pump chamber is defined between a piston and cylinder, one of these (usually the piston) moving with the plunger. Pump chambers with deformable walls may also be used. Pump dispensers of the moveable-nozzle type, in which the discharge channel and outlet opening are comprised in the plunger, and of the fixed-nozzle type in which the discharge channel and outlet opening are part of or fixed relative to the pump body, are both possibilities. For dosing of oral compositions such as medicines a fixed-nozzle dispenser has advantages because the outlet can more easily be held steady.

What we propose is that the dispenser discharge outlet has an outlet closure valve with a closure mechanism comprising a closure member which in a closed position closes the discharge outlet. The dispenser also comprises an outlet attachment which defines an outlet conduit having a nozzle opening. The outlet attachment can be coupled to the dispenser at the outlet opening, by means of suitable coupling structure. Typically this comprises respective interfitting formations or coupling elements of the outlet attachment and of the dispenser adjacent to the outlet opening.

The outlet attachment comprises an actuating portion which, in the coupled condition, engages the closure mechanism of the dispenser to hold the closure valve in an open condition. In this open condition the dispenser discharge outlet is in fluid communication with the outlet conduit and nozzle opening of the outlet attachment, so that fluid product can be dispensed from the dispenser through its own outlet opening and thence through the outlet attachment.

When the outlet attachment is uncoupled from the dispenser—moved to an uncoupled condition or position—the closure mechanism is operable to move to a closed condition in which the closure member of its closure valve closes the outlet opening. Preferably the closure member is biased e.g. by a spring so that the closure mechanism automatically closes the dispenser outlet opening when the outlet attachment is uncoupled and removed.

The preferred closure mechanism is mechanically operated and not responsive to forward fluid pressure in the dispenser to open it. Indeed it may be arranged so that forward fluid pressure tends to keep it closed.

Preferably the actuating portion of the outlet attachment acts to drive the closure valve closure member back, i.e. in an upstream direction, out of its closed position. The actuating portion may act directly on the closure member, usually by direct contact, e.g. on a portion thereof exposed at the dispenser outlet opening. As mentioned, this may be against a forward or outward spring bias of the closure member so that when the outlet attachment is removed, or in general moved to a disengaged, uncoupled or non-actuated condition or position relative to the dispenser outlet, the closure member pushes out to re-close the outlet opening.

Preferably the closure member in the closed position is at the outlet opening. It may occupy the outlet opening at least substantially flush with, or projecting out beyond, a surround surface of the outlet opening so that after removal or disengagement of the outlet attachment, any residual fluid product is either enclosed in the dispenser behind the closure member—and so protected against drying out, contamination of the like—or is on the exterior of the dispenser so that it can be easily wiped or washed away, or else is in or on the separate outlet attachment which, being typically a discrete removable tubular component, separable from the dispenser body, can easily be cleaned or replaced.

The dispenser outlet opening may be in a projecting nozzle, outlet stub or spigot of the dispenser, onto, over or into which the outlet attachment fixes. [The word "onto" herein is used hereinafter to cover all of these possibilities for this fixing, except where specific context indicates otherwise.] Alternatively the outlet opening could be in a flush face of the dispenser, or even recessed, although (depending on the mechanism and disposition of the closure member) this latter might make cleaning and/or securing of the outlet attachment more difficult.

The outlet attachment, which may also be considered as a discrete or removable extension tube or hygienic mouth adaptor for the dispenser outlet, is preferably a generally tubular component with a socket or plug portion shaped to fit conformingly onto or into a corresponding stub outlet, spigot or socket of the dispenser. Preferably this fitting part of the dispenser also defines the outlet opening. The actuating portion of the outlet attachment may be provided in the tube thereof, e.g. moulded in one piece with the tube. It may be a rearwardly-directed formation e.g. projection positioned generally in the middle of the tube opening. A suitable mounting of the actuating portion is by means of one or more support elements or spokes connecting to an adjacent wall of the tube. When the outlet attachment is moved or put into the actuating or docked position on the stub outlet or spigot of the dispenser, the rearwardly-projecting actuating portion pushes the closure member of the dispenser closure mechanism back out of its blocking relation with the outlet opening, preferably against spring bias, to an open position.

The actuating portion of the outlet attachment should be non-blocking, i.e. shaped, dimensioned and positioned so that it does not itself block the outlet opening. It will be understood that a similar effect could be achieved by having a forward non-blocking projection of or on the closure member, which can be engaged and pushed back by the actuating portion of the outlet attachment which may then not need to enter the dispenser outlet opening. However this is normally less preferred because a part projecting from the outlet opening is more liable to damage.

Considering the closure mechanism, the closure member may be in the form of a front (outer) plug cooperating with a rear (inner) spring, deformed against its resilience, e.g. compressively, when the plug is pushed backwards. A compression spring may engage a rear abutment in the outlet structure. Any kind of spring may be used, but a preferred embodiment has one or more flexible rearward legs which bend against their resilience as the closure member is moved to the open position. A rear end of the or each leg may engage beside or around a central flow opening of the outlet structure, upstream of the actual outlet opening. The closure member may be formed integrally with the spring or with one or more elements thereof.

To facilitate assembly of the closure mechanism, preferably a discrete nozzle stub or spigot component defining the discharge outlet is fixed onto a body of the dispenser, defining between them a closure mechanism cavity for the closure mechanism or part thereof, e.g. spring and/or closure member.

For guiding the closure plug, it may be slidable in a guide portion of the discharge channel immediately upstream of the outlet opening, having guide portions to contact the plug separated by flow clearances so that liquid can pass forward around the plug until it reaches its foremost, closed position.

The outlet attachment may secure to the dispenser body by any suitable coupling structure or retaining mechanism, e.g. a thread, push fit, interference fit, locking cams, bayonet-type fitting, wedge or taper fit etc. The coupling needs to retain the outlet attachment sufficiently positively to keep it in place and to keep the closure mechanism open. Additional options for this are described below.

The dispenser body portion to which the outlet attachment fits may be on the plunger of a moveable nozzle dispenser, or on a fixed part of a fixed-nozzle dispenser.

The outlet attachment may be shaped at its nozzle opening for suitability for oral dosing, i.e. to be put in the mouth. Desirably it has a surround surface tapering towards the nozzle opening, and which is smoothly curved or rounded i.e. without angles, edges or corners at this part. It may have circular symmetry around the nozzle axis. Or, it may have a flattened or beak-like outer form. In the latter case the coupling or retaining mechanism which holds the outlet attachment on the dispenser may then be alignment-selective, e.g. to provide only one or two possible coupled alignments of the nozzle attachment relative to the dispenser.

The dispenser may have a forwardly-acting outlet valve positioned upstream of the closure mechanism, e.g. an outlet valve of known or conventional type preventing in-flow, for assuring re-filling of the pump chamber on a plunger recovery stroke.

Preferably the dispenser is of the "airless" type in which the product is dispensed from a container with a follower piston or from a collapsible container (or collapsible container liner) so that the container space (product space) remains essentially full of product.

One or more of the characteristic outlet attachments (separable/discrete nozzles) may be provided with the dispenser. More than one differently-sized or shaped nozzle attachment may be provided for use with a single dispenser, e.g. for dosing different sizes/ages of children. The dispenser may have an outer cover cap to cover the outlet structure. It may be arranged that the cover cap will not fit over the outlet structure with the outlet attachment in the coupled or actuated position. This encourages detachment or uncoupling of the nozzle after use, improving security.

As mentioned, the idea is particularly useful with oral compositions such as oral medicines, for humans or animals. The volume of a pump chamber corresponding to a unit dosage can be determined accordingly, and for human use would usually be less than 20 ml, usually at least 2 ml, more usually not more than 10 ml, e.g. 10, 5 or 2.5 ml.

Proposals Herein

An important issue with dispensers for oral products for children is child-resistance, so that a child cannot itself use the dispenser. Especially with medicines this could be extremely dangerous.

Other important issues with dispensers for oral products such as medicines include tamper protection and tamper-evidence, for obvious reasons. Here we make proposals for tamper protection and tamper-evidence.

Other additional proposals herein include new closure mechanisms for the outlet and new coupling mechanisms for the outlet attachment.

(1) Security Mechanism/Child Resistance

Especially with medicines, security and child resistance are important. Bottles and jars used to contain medicine conventionally have child-resistant closures. It is desirable and may indeed be a requirement to provide corresponding security in a pump dispenser of the present kind. This requires novel measures, because there might be no lid or cap in the ordinary sense. However, it may be implemented in the connection structure or coupling structure for connecting the outlet attachment (nozzle attachment) to the dispenser at or adjacent the dispenser outlet which has the closure valve.

The connecting or coupling structure provides a preliminary engagement condition from which a completion movement is necessary to move to the coupled condition (operational fluid communication, closure valve open). The preliminary engagement condition may be a stable holding position, as described below, or it may be the initial engagement of the components as they are brought together for coupling. The completion movement may be of any of the kinds discussed below. Most preferably it is a straight push of the outlet attachment onto the dispenser outlet, e.g. an axially-aligned sliding movement onto a spigot.

Aspects of these proposals are set out in the claims. In a first aspect the invention provides a dispenser for fluid product, the dispenser comprising a dispenser body, the dispenser body comprising a discharge outlet defining an outlet opening and an outlet closure valve with a closure mechanism comprising a closure member which in a closed position closes the discharge outlet;

an outlet attachment, the outlet attachment defining an outlet conduit having a nozzle opening, and which can be coupled to the dispenser at the discharge outlet (6) by a coupling structure, the coupling structure comprising respective coupling elements of the dispenser body and outlet attachment which interfit, and so that in a coupled condition fluid product can be dispensed from the dispenser through the outlet attachment;

said coupling structure providing that the coupling of the outlet attachment to the dispenser comprises a completion movement to reach said coupled condition in which fluid product can be dispensed from the dispenser through the outlet attachment;

the dispenser comprising additionally a security mechanism, the security mechanism comprising respective cooperating elements of the dispenser body and outlet attachment, and the security mechanism being controllably adjustable between a blocking condition, in which said cooperating elements co-operate to block the completion movement, and an access condition in which said cooperating elements allow the completion movement.

According to this general proposal, the dispenser comprises a security mechanism provided by cooperating elements of the dispenser and outlet attachment, which are controllably adjustable between a blocking condition which blocks the completion movement and an open or access condition which allows the completion movement. This adjustment may be by means of a control, that is to say, a control member or control element, which can be adjusted or moved to a predetermined release condition (e.g. release position) corresponding to the open condition of the security mechanism. Preferably the control member or element is on the dispenser because it is preferred that the outlet attachment be a simple component without moving parts.

In preferred mechanisms the coupling structure includes an entry path or track of the dispenser body which receives a complementary portion of the outlet attachment. It may be an opening or recess of the dispenser body casing or housing, receiving a projection on the outlet attachment. Optionally more than one such entry path or track (and corresponding projections) may be provided. The entry path or track may be disposed so as to be covered by the outlet attachment when the latter is in the coupled condition. Thus, in the preferred embodiments where the outlet attachment is a tapering nozzle with a wide base, one or more entry openings of the dispenser body may be provided at locations which are covered by the nozzle attachment base.

For provision of the blocked condition, the safety mechanism may comprise a movable element, such as a retaining formation or detent formation, positioned e.g. adjacent the mentioned path or track for the projecting portion of the outlet attachment. Desirably it is on the interior of the dispenser so as not to be visible (or not entirely visible) from the outside even when the outlet attachment is removed. This improves child-resistance. The movable member or formation can be operatively connected to a control member as mentioned above. The control member may be e.g. a push button or pad, lever or slider. In the blocked condition, the detent or retaining formation engages a complementary or corresponding portion or formation on the relevant part (e.g. projection) of the outlet attachment and prevents it from moving into full engagement or connection. It may simply block the entry path or track. It may be movable transversely relative to the entry path or track. Alternatively a detent or retaining formation may be static, and the control member guides movement of the portion (e.g. projection) of the outlet attachment relative to it, so as either to clear it or to be blocked thereby.

A primary purpose of the security mechanism is to prevent the completion movement which couples the nozzle and opens the closure valve. Additionally or alternatively however it may operate to hold (or help hold) the outlet attachment in the coupled position. For example the above-mentioned projecting portion of the outlet attachment may have a rearwardly- (outwardly-) directed abutment surface, and after coupling of the outward attachment the security mechanism may be operable such that a detent or retaining formation thereof engages this abutment surface to hold the outward attachment against removal. Of course, this may be the same detent or retaining formation which is used to control its coupling.

Preferably the security mechanism includes means such as a spring to bias the detent or retaining formation to the blocking condition. This improves security against unintended or unauthorised coupling. It may also serve to make automatic the function of retaining the coupled nozzle against removal.

The coupling arrangement may include a biasing spring or ejector spring disposed to push the outlet attachment out of the coupled condition. Again, this bias improves security. A separate spring may be provided. Or, it may be a spring comprised in the closure valve, for example a spring which pushes outwardly a closure element such as a closure plug or closure sleeve, the closure element pushing in turn on the actuator portion of the outlet attachment. Thus, retention by a detent of the security mechanism may be the only means holding the outlet attachment in place in the coupled condition.

Holding Engagement

A further proposal is that the coupling structure or connection structure may provide for a preliminary holding engagement of the nozzle attachment, in a holding position on or adjacent the dispenser outlet, with the nozzle supported stably in position adjacent to the outlet opening, but not opening the outlet closure valve, i.e. not in the above-mentioned coupled condition or coupled position. This may be easily be arranged e.g. when the coupling structure includes interfitting tubular portions of the outlet and nozzle attachment which slide or screw onto one another.

For example the outlet attachment may be slid partly onto or into a tubular fitting structure of the dispenser body, such as structure at or surrounding the outlet, to be held stably in position for shipping and/or sale, thereby showing the general nature of the device without compromising security of the contained product. The outlet attachment (e.g. nozzle attachment) is movable from the holding position to the coupled position (i.e. closure valve open) by a completion movement (relative movement between outlet attachment and dispenser, or between outlet attachment and dispenser outlet). The corresponding completion movement may be any kind of movement e.g. a turn around the nozzle axis, tilt, linear slide (axial and/or lateral), screw or any combination of these. As discussed below, a complex movement may give valuable child-resistance. However, we prefer a simple movement, such as a direct axial push, as the completion movement. If a suitable security mechanism is provided, such as for child resistance, the holding position and coupled position may be close e.g. not more than 5 mm axial distance. As described above, a suitable security mechanism e.g. child resistance mechanism can be provided to prevent unintended or unauthorised coupling of the outlet attachment.

(3) Protective Cover

It is well-known for dispensers to include certain protective covers such as nozzle plugs, tear-off wraps and the like, to avoid contamination and/or leakage of the contents e.g. during shipping. Mechanisms for lock-down or lock-up of pump plungers are also used for these reasons, primarily with moveable-nozzle pumps. The present invention may be used with movable-nozzle pumps, but is preferably used with a fixed-nozzle pump.

Especially in the context of medicine such product security is highly important, and desirably is provided even when an outlet attachment is present in a holding position.

In the case of a fixed-outlet pump (i.e. where the dispenser outlet does not move with the plunger) we propose a removable protective cover which overlies the top of the plunger and adjacent portions of the dispenser head housing, thereby preventing or inhibiting depression of the plunger.

Where an outlet attachment is provided in a holding position as proposed above, we also propose a protective cover on or over the outlet attachment which again overlies or engages parts of the dispenser body casing, shell or housing adjacent the outlet attachment thereby preventing or inhibiting movement (simple pushing) of the outlet attachment onto the dispenser e.g. on a completion movement as discussed above. Where the outlet attachment is provided separately, the outlet formation of the pump body may have a protective cover instead. This cover desirably closes off the nozzle opening. Desirably it conforms to the outside of the nozzle attachment. It may engage or grip the outlet attachment so that the outlet attachment comes away with (e.g. inside) the cover when the cover is removed. For example it may have an outlet It may be a single-use cover.

Preferably a single protective cover element may be used to cover both the outlet attachment (or pump body outlet) and the plunger.

Another possibility is a protective cover for a control member of a child-resistant security mechanism as proposed above, thereby preventing release of a mechanism allowing the outlet attachment to be moved to a coupled condition. Again, if such a protective cover is provided it may be individual, or combined (e.g. in one piece) with a protective cover for a plunger and/or outlet attachment or outlet as discussed above.

In a preferred embodiment a plastics component is used as protective cover for the above purposes. Preferably it is flexible, and can be pulled away from the dispenser head. It may be reusable.

(4) Tamper-Evidence

It is known in dispensers to provide that the plunger cannot be operated for dispensing until some protective cover, connector or other component preventing initial use has been visibly removed, destroyed or damaged. Such tamper evidence is desirably provided in the present dispenser. This may be by any conventional adaptation. We particularly propose a tamper-evident mechanism in which one or more protective covers as discussed above is attached to the dispenser through a frangible connector which must be broken e.g. pulled off or torn away, in order to remove the protective cover(s). Attachment/anchorage to the dispenser body may be by a barbed element secured through an opening in the case or housing of the dispenser body. It is possible to provide that the sacrificial element is separable from the protective cover(s) so that the latter may be reused.

Another option for tamper evidence is to connect an external control of a child-resistant security mechanism (e.g. as discussed above) to the adjacent dispenser structure by means of a removable element, e.g. a frangible element, which must be removed or broken in order to operate the security mechanism so that the dispenser can be used.

BRIEF DESCRIPTION OF THE DRAWINGS

These proposals are now illustrated by description of examples, with reference to the accompanying drawings in which:

FIG. 7 showing the nozzle mounting structure and nozzle when fully detached;

FIGS. 8 and 9 being enlarged vertical sections at an actuating member during coupling, and FIG. 10 showing an engaged coupling control tab from inside;

FIG. 11 being a fragmentary cross-section just off-axis adjacent the outlet, viewed obliquely, with the nozzle in a pre-mounted or holding position;

FIG. 12 is an axial cross-section of the top of the dispenser in the same holding position;

FIG. 13 is similar to FIG. 11 but showing a release switch in the open or release position;

FIGS. 14 and 15 are views from beneath the detached dispenser head module, showing respectively open/released and closed/locked positions of the child-resistant nozzle attachment mechanism, and FIG. 16 is an axial cross-section of the top of the dispenser with the nozzle fully coupled;

FIG. 19 showing the inside of the removed cover holding the nozzle,

FIG. 20 being an axial section of the dispenser showing the nozzle on the dispenser in a holding position with the nozzle cover portion on it, as immediately before removal for use, and FIG. 21 is a radial section through the cover and nozzle tip showing circumferential alignment formations on a grip coupling between them.

DESCRIPTION OF THE SELECTED EMBODIMENTS

Figures 1, 2:
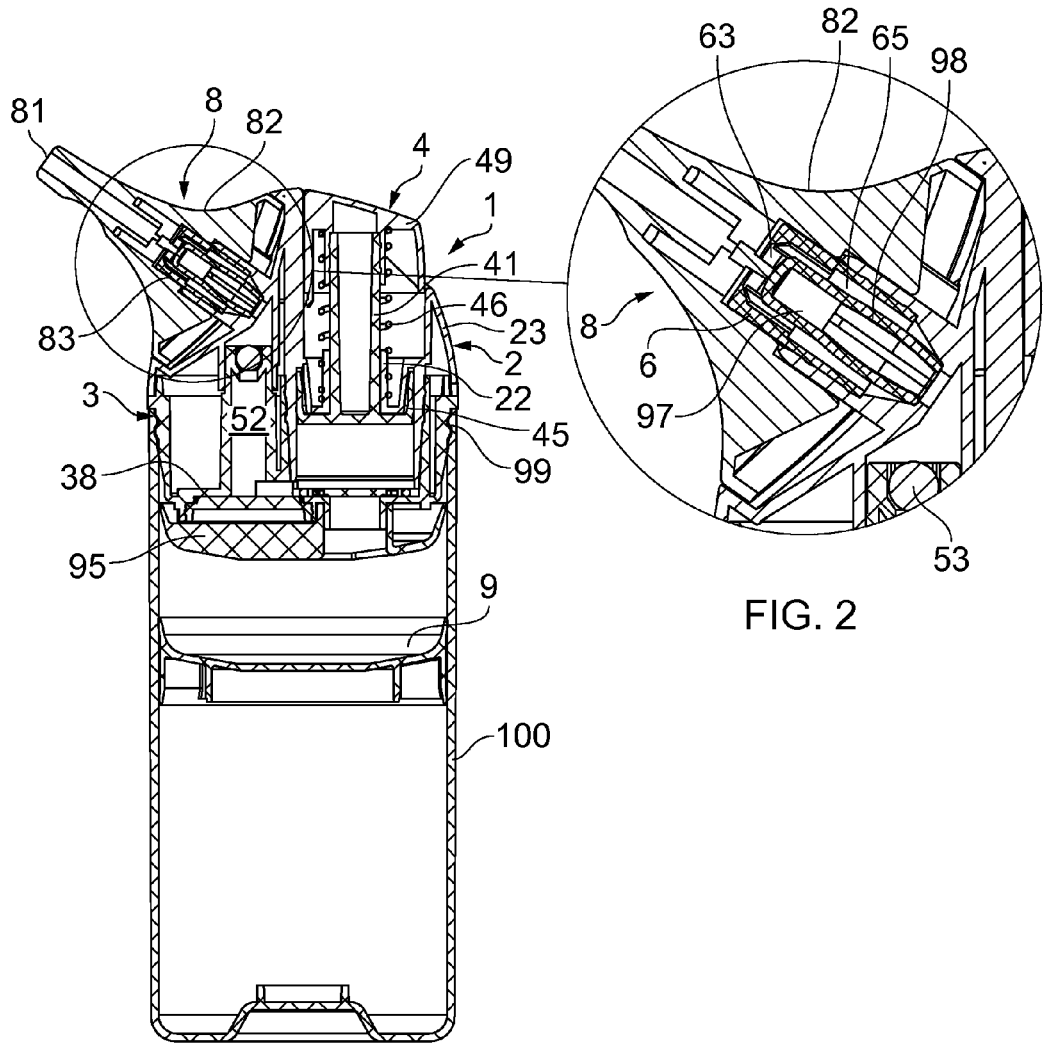
FIG. 1 shows an axial cross-section of a first embodiment of fixed-nozzle dispenser for oral dosing, with a nozzle attachment in the fully coupled (connected) position.
FIG. 2 is an enlarged view of nozzle mounting structure in FIG. 1.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Referring to FIGS. 1 to 5, a fixed-nozzle dispenser for dosing medicine to children comprises a product container 100 with snap ribs 99 around its top opening into which a pump unit 1 is fitted. A follower piston 9 is provided in the container 100 and rises as product is dispensed. The dispenser has a body mounting element 3 which plugs down into the container opening. The mounting element 3 is generally bowl-shaped, with an outer surround wall 34 which plugs into the container neck and a floor 38 with an eccentric inlet opening 31 controlled by an inlet valve 54. At a rear position, above the inlet opening 31, the mounting element 3 has an upwardly-extending socket 32 for a pump cylinder. At a front position an upward outlet tube 35 projects up from the floor 38 and houses an outlet ball valve 53.

A horizontal outlet channel 36 connects the vertical outlet passage 52 in the tube 35 with the pump chamber space 5 to the rear, and is closed off from beneath by a closure plate 37.

Figures 3, 4:
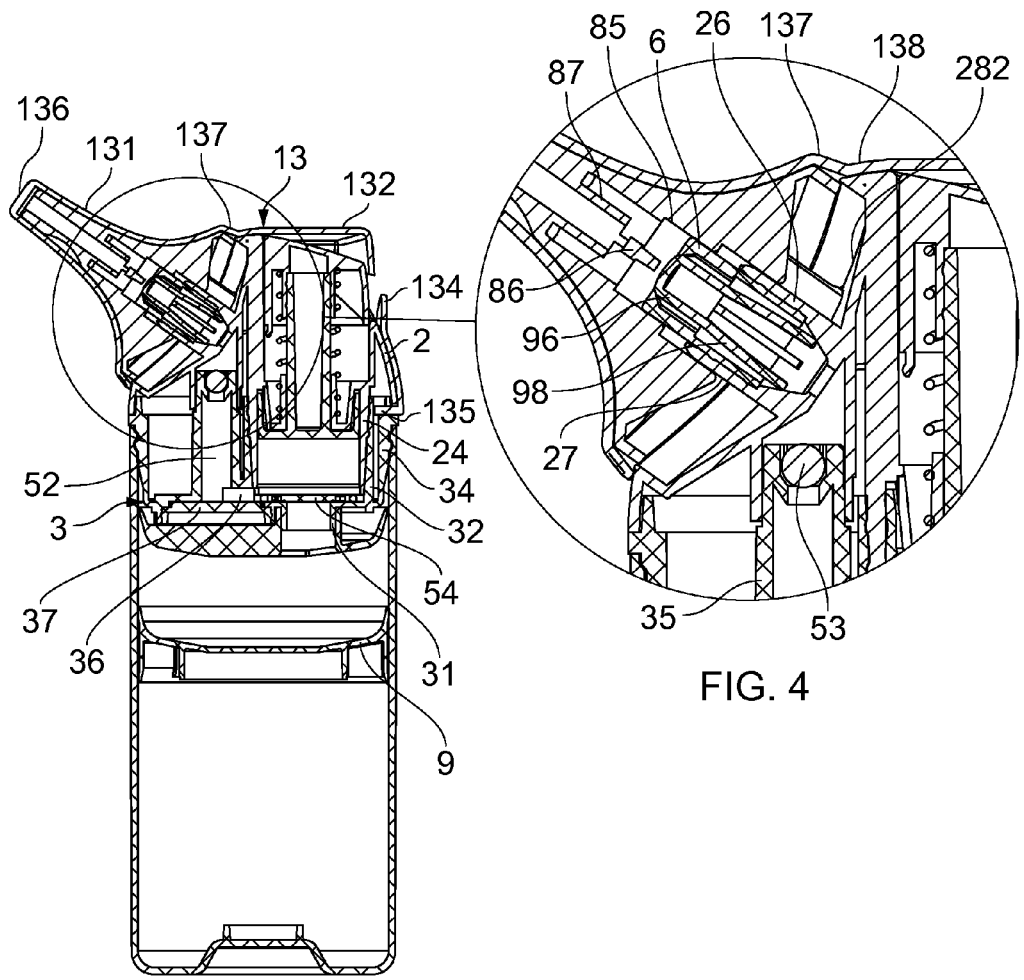
FIG. 3 and FIG. 4 are views corresponding to FIGS. 1 and 2 but with the nozzle in a pre-mounted or holding position as for shipping or sale, with tamper protection and tamper-evident fittings in place.
Figure 5:
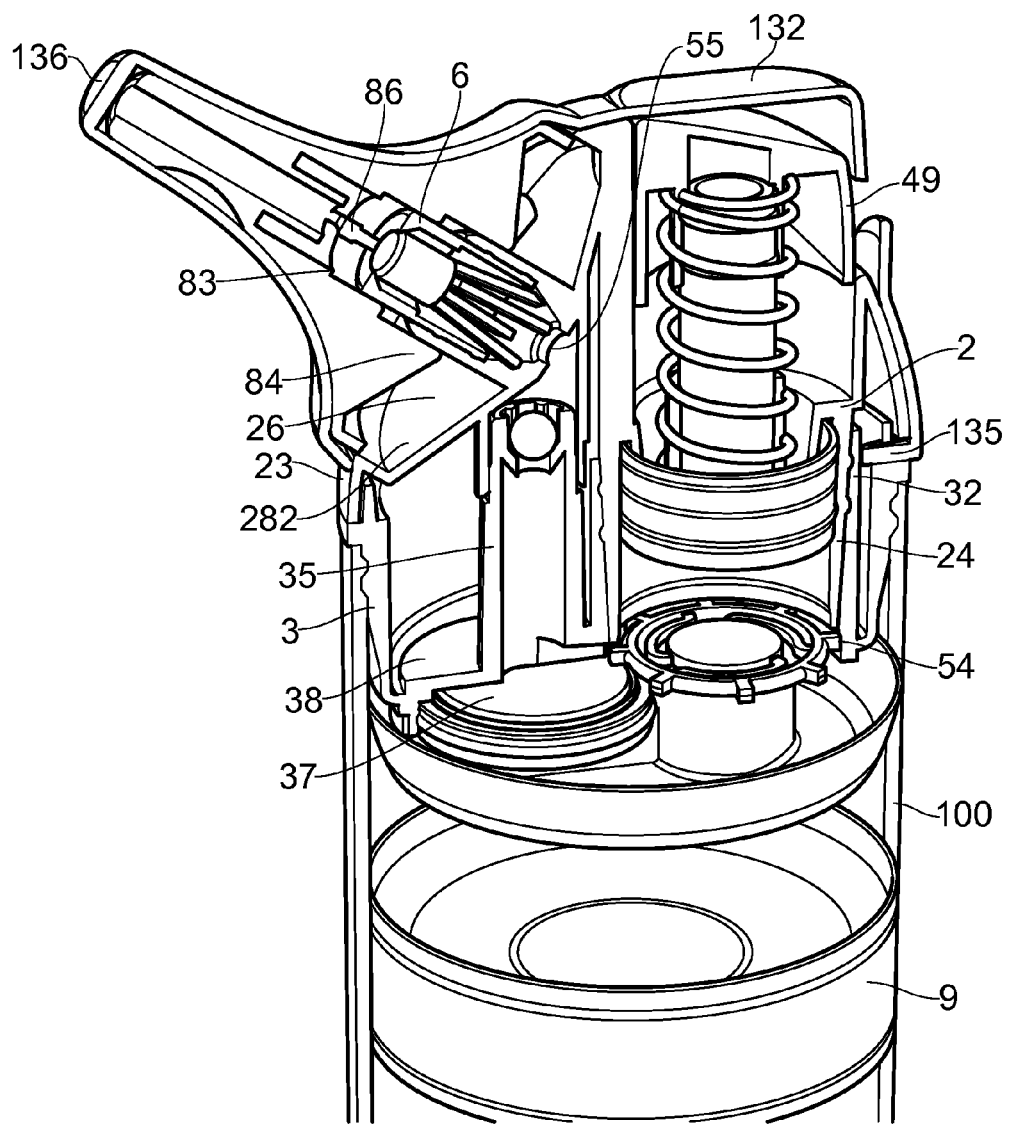
FIG. 5 is a perspective axially-sectioned view corresponding to FIG. 3, showing the components in three dimensions.
Figure 6:
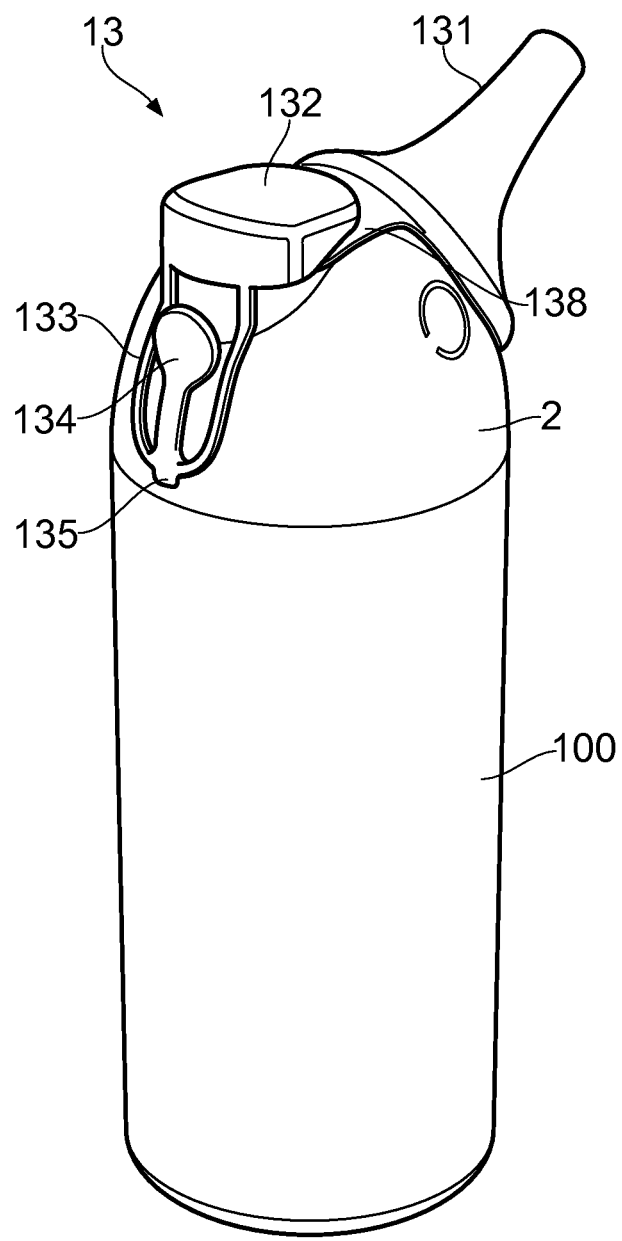
FIG. 6 shows the first embodiment from the rear and one side to show the tamper-protection and tamper-evident fittings.
Figure 7:
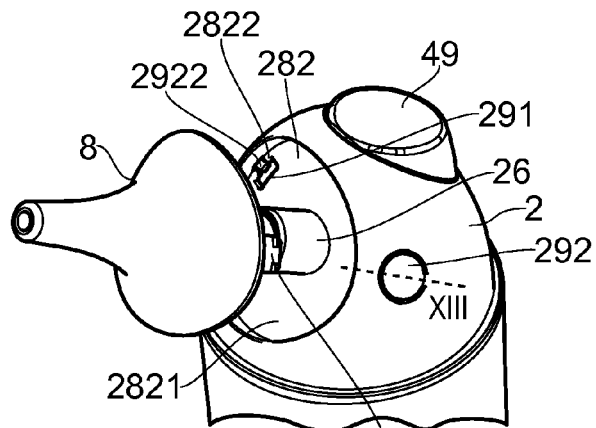
FIGS. 7 to 10 show details of a child-resistance feature associated with completing coupling of the nozzle attachment [and showing a slight variant of structure relative to FIGS. 1 to 6]

FIGS. 1, 3 and 5 also show an air trap component 95 plugged into the underside of the base plate floor 38; this is optional and may be e.g. as described in our EP-A-2353727.

A top body element 2 fits down onto the body mounting element 3 to complete the pump flow system. The top body element 2 includes at the rear a pump cylinder 24 which plugs down into the cylinder socket 32 to define the pump chamber 5. At the front it has a downwardly-projecting socket 25 which connects down to the outlet tube 35 and leads up to a discharge outlet structure described in more detail below. The top body element 2 also has a surround shell 23 which fits down onto an upward collar of the mounting element 3 to enclose the flow control components. At the back of the pump this shell has a guide recess 128 in which a plunger button 49 of a pump plunger 4 is operable. This plunger button is on the top end of a piston stem 41 carrying a piston 45 at its bottom end. The piston 45 operates in the cylinder 24, the top wall of which projects inwardly connecting to an integrally-formed tubular stem guide 22. A return spring 46 between the button 49 and cylinder 24 urges the plunger button to the top position.

The volume dispensed per stroke of the plunger 4 may be e.g. 2.5 ml.

The characteristic outlet structure is described initially with reference to FIGS. 1, 3 and 4. The vertical outlet passage 52 communicates through top exit hole 55 to the exterior of body shell 2, emerging in the centre of a shaped socket recess 282. It emerges through a stub mounting 26 having a cylindrical outer surface 27 constituting a securing formation for a nozzle (outlet) attachment described below, and small snap formations on the inside.

A stub nozzle 6 is plugged into the stub mounting 26. This stub nozzle 6 is a tube with a restricted tip discharge outlet opening 63 at the front end of a relatively enlarged tip flow section 66. Trapped in the cavity 65 inside the stub nozzle 6 is a one-piece closure valve element 96, with a front cylindrical plug portion 97 fitting with flow clearance into the parallel-sided flow section 66 at the front of the stub nozzle, and a set of spring legs 98, formed integrally with the plug 97 as a single moulding, projecting back and seating in a conical depression around the flow exit opening 55 of the body shell 2. The parts are dimensioned to give slight pre-bending of the legs 98, so that (FIG. 4) the plug 97 is urged forwards to the outlet opening 63 where it fits closely in that plain circular front opening and blocks flow. Rearwardly of the opening 63 the flow section 66 has flow channels or clearances in its walls so that liquid can flow out past the plug 97 when the plug is pushed back, as seen in FIG. 1, while keeping it central.

A removable nozzle attachment 8 fits over the stub nozzle 6. The nozzle attachment 8 (outlet attachment) is a one-piece moulded plastics part. It generally tapers from a wide base part adjacent the dispenser body in use to a narrow tip with a nozzle opening 81. It is generally of circular cross-section, and its outer surface 82 widens and diverges rearwardly at gradually increasing angle to a circular rear edge. At the rear edge the divergence stops and there is a substantially cylindrical rearwardly-projecting skirt 28282 which fits closely but without interference into the circular periphery of a nozzle-receiving recess 282 of the dispenser body 2: see FIG. 2. Inside the nozzle attachment 8 a substantially uniform narrow bore extends back to the nozzle opening 81 to provide an outlet conduit. In the rear of the nozzle attachment 8 at the centre, an inner rear attachment tube section 83 projects and has a cylindrical inward surface which fits closely around the outlet nozzle and nozzle stub 6,26, in a sliding fit. These central joint formations of the attachment 8 are supported rigidly relative to the outer casing 82 thereof by means of a set of radial fins 84 (e.g. eight, in this embodiment).

The narrow exit conduit has a rear tubular extension 87 projecting out into the central cylindrical space, and supporting a rearwardly-projecting central point or pusher 86 (actuating structure). The supporting structure for this may be a simple transverse bar or one or more spokes, leaving the entrance to the tubular conduit open for flow.

The cylindrical stub and socket formations are dimensioned such that the attachment 8 can be stably supported thereby in the holding position seen in FIGS. 3 and 4.

FIGS. 1 and 2 show how, in the fully-coupled position, the nozzle surround lies flush with the shaped head shell of the dispenser. The edge of the nozzle surround has a substantially cylindrical rearwardly-projecting skirt which fits closely into the complementary circular rim of the nozzle-receiving recess of the dispenser head, having the nozzle outlet stub at its centre.

FIGS. 3 and 4 show the preliminary or holding position for the nozzle, with the tubular fitting components engaged, so that the nozzle is held stably on the mounting, but (see FIG. 4) with the closure mechanism still shut and the actuating member not yet pushing in the closure member. In this position the skirt of the nozzle surround still just reaches the edge of the corresponding dispenser head recess, shielding the internal structure from sight and from interference. The length of the skirt might be e.g. from 2 to 5 mm, corresponding substantially to the length of the completion stroke required to push the nozzle from the holding position to the fully coupled position.

FIGS. 3 to 6 also show a protective overcap 13 with a tamper-evidence feature. The overcap has a nozzle cover portion 131, a plunger button cover portion 132 and a frangible link 133 at the rear. The nozzle cover and button cover 131,132 are connected via a flexible connecting strip 136. The frangible link connects to the back of the button cover. The bottom end of the frangible link is connected permanently to the back of the dispenser body casing 2 by a barbed projection 135 (see FIGS. 3 and 5) pushed irreversibly through a small hole in the dispenser casing 2. It carries a tear-off tab 134 by which, on first use of the dispenser, it can be broken away from the barbed anchor 135 and pulled off upwardly and forwardly to uncover the plunger button and nozzle attachment.

The nozzle cover portion 131 is shaped to closely complement the exterior of the nozzle attachment 8 in the holding position (FIGS. 3, 4). It has a blind tip 136 to protect the interior of the nozzle or spout 8. It also has an angled push-resistant wall portion 137, extending around the base of the attachment 8 adjacent the dispenser body 2 and approaching more closely to perpendicularity thereto, to resist inward pushing at the nozzle attachment 8. This may complement the action of a child-resistant or security mechanism described below.

The button cover 132 is shaped to fit closely on top of the plunger button. By its integral formation with the flexible connecting strip 136, which constitutes a surround portion resting against an adjacent fixed part of the dispenser body, it prevents depression of the plunger button until the protective overcap has been removed.

In the illustrated construction, removal of the protective cap 13 leaves the nozzle attachment in place, ready for actuation. An alternative is to provide a retaining engagement between the nozzle cover portion 131 of the cover 13 and the nozzle attachment 8, so that the nozzle attachment 8 is pulled off when the protective cover is pulled off. This might be e.g. by means of a inward plug formation on the inside of the tip wall 136 (not shown here, but see FIGS. 19 to 21 below) engaging in the nozzle opening. A virtue of this option is that by removing the nozzle attachment 8, it alerts the user to the need for special coupling of the nozzle before use.

Figure 17:
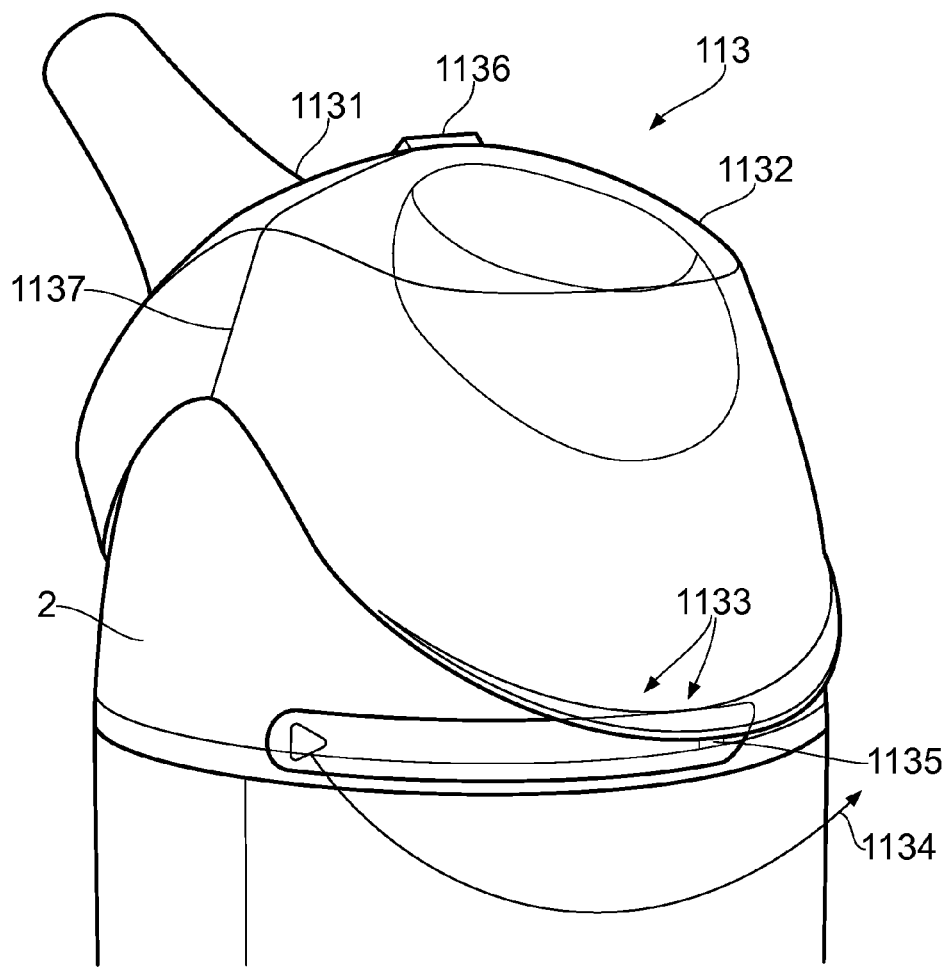
FIGS. 17 and 18 show a fourth embodiment with an overcap different from that of FIGS. 3 to 6.
Figure 18:
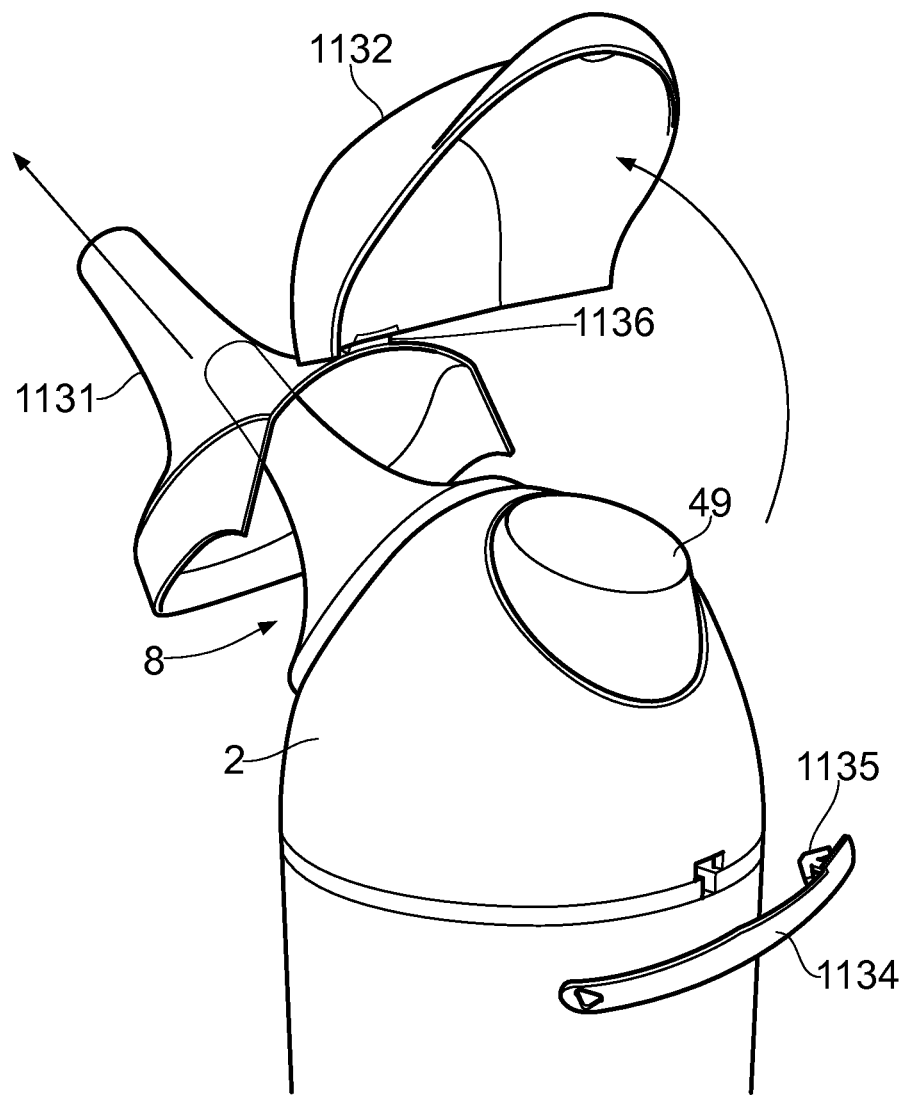

FIGS. 17 and 18 show an alternative embodiment of protective cover or overcap. The main elements of the overcap 113 are broadly the same, i.e. a front nozzle cover portion 1131 closely conforming to the outside of the nozzle attachment, an intermediate plunger button cover portion 1132 covering the plunger button and adjacent surround surfaces of the dispenser body 2, and a rear tear-off portion 1134 with a permanent anchor 1135 into the back of the dispenser body, connected by frangible joints 1133 to the back of the protective cover or overcap 113. In this embodiment the overcap has flank regions extending down either side of the dispenser body 2, giving stronger resistance to pushing on both the nozzle and the plunger button. To allow for the corresponding removal of the overcap 113 with flexion but without damaging it (so that it can be reused), the nozzle cover 1131 and button cover 1132 are connected only at a central hinge 1136, otherwise being discrete along a joint line 1137 (FIG. 17). The tear-off strip 1134 has a free end projecting laterally to one side, to be pulled away in the sense indicated in FIG. 17. The anchorage 1135 to the body shell 2 and the frangible links 1133 to the main cap 113 are all adjacent one another at the other (central) end of the tear-off strip 1134, so that when pulled away for first use, it pulls free of the cap 113 in the same action, leaving (as shown in FIG. 18) the hinged two-portion cap 113 available for reuse. Optionally (as in the previously-described embodiment) the nozzle cover portion 1131 may be adapted to engage and pull off the nozzle attachment 8 as it is itself removed.

With the nozzle attachment 8 removed, it will be understood that the outlet opening 63 is closed off essentially flush by the valve plug 97 and can easily be wiped or washed clean. The valve plug 97 prevents product from being sucked from the dispenser when the nozzle is not fitted or in the holding position, and also isolates from the air any residual product in the discharge channel 52, preventing drying and contamination. The intention is that after each use the user should wholly remove and clean the nozzle attachment 8.

Next, two embodiments of security mechanism (child-resistant mechanism) are described, and an alternative embodiment for the closure valve and associated coupling mechanism.

FIGS. 7 to 10 show a security mechanism for a dispenser substantially as shown in FIGS. 1 to 5. There is a slight variant construction for the nozzle attachment 8, which has no rearward cylindrical skirt at its rear edge. Instead, the parts are dimensioned so that in the holding position the rear edge is approximately flush with the envelope of the dispenser body 2, while in the coupled position (see FIG. 9) the edge is relatively depressed. This is just a variant, not in itself relevant to the security mechanism now to be described.

Figure 8:
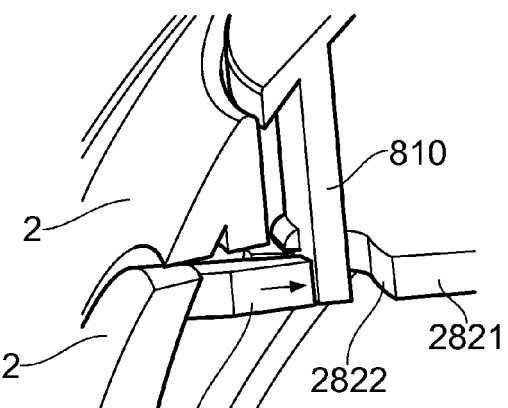
Figure 9:
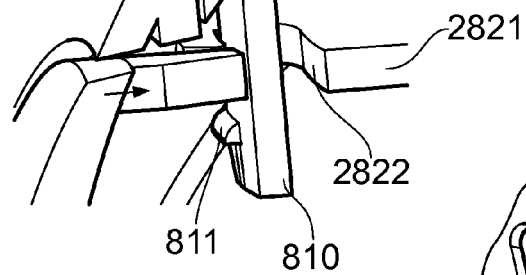
Figure 10:
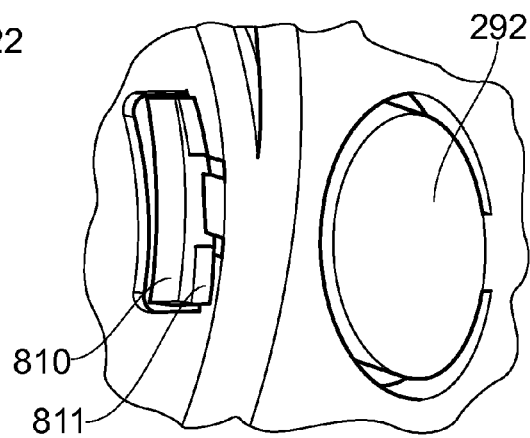

The security mechanism is to prevent the nozzle from being easily pushed to the coupled (open) position, either directly from a detached state or from a preliminary holding position. The back of the nozzle 8 has two rearwardly-projecting tabs 810, to be received in corresponding openings 2822 in the back wall 2821 of the depression 282 in the dispenser body 2 that receives the base of the nozzle. With the nozzle in position, (preliminarily or fully) these engagements are covered and invisible. As seen in FIGS. 8 to 10, each tab 810 is generally a straight lug of more or less rectangular form, but has near its tip a pair of spaced nibs 811. In this embodiment the nibs 811 are formed with a square (perpendicular) rear face and a ramped or rounded front (outward) face.

The body wall openings 2822 are near the edge of the depression 282 and associated with each is a push button or control member 292 in the outer side wall of the body shell 2. In this embodiment the control buttons 292 are formed integrally with the body wall with an integral hinge portion, but they may be a discrete element. Projecting inwardly from the inside of each control button 292 is a pusher element 2922, directed at the middle of the wall opening 2822 and narrow enough to pass between the spaced nibs 811 on the corresponding nozzle lug 810.

FIG. 8 and FIG. 10 show the preliminary holding position. The rearward square face of the nib 811 rests against the edge of the wall opening 2822, preventing the nozzle from being pushed further in. Inward pressure on the control button 292 (FIG. 2) bends the tab 810 slightly away from the edge of the wall opening 2822, so that the nibs 811 can pass through to the coupled position shown in FIG. 9. In this embodiment, two control buttons 292 must both be depressed to couple the nozzle attachment. This requires substantial coordination, and gives a high degree of child-resistance. However a single such mechanism will have a corresponding effect albeit to a lesser degree.

In this embodiment the frictional force at the outlet coupling is sufficient to hold the attachment 8 in position during use. The tab nibs 811 can be pulled out over their ramp surfaces without needing to operate the control buttons 292 again. This assumes little or no spring force pushing the nozzle out. Such a spring force may be desirable, in which case it will be understood that the nibs 811 could be formed square on both sides, and the nozzle will be retained unless the mechanism is positively released by pushing the buttons 292 again.

FIGS. 11 to 16 show a further dispenser embodiment with a different security mechanism (child-resistant feature) and a different kind of closure valve.

The child-resistant safety mechanism here is designed to stand higher forces than the previous embodiment. It can also hold the nozzle attachment 108 in the coupled position even against a substantial outward spring force from the closure valve.

The nozzle 108 has, projecting rearwardly from near its bottom edge, a coupling control projection 8200. In this embodiment the coupling control projection is substantially cylindrical in form, having a flat leading face 8201 and a side notch or shoulder 8202 on the lower side. It is received in an entry opening 227 through the wall of the dispenser body 2, in the nozzle-receiving recess which generally resembles that of previous embodiments. However, the entry opening 227 in this embodiment is at the bottom edge of the recess, near to the front of the dispenser underneath the nozzle. Access or mobility of the control projection 8200 at the entry opening 227 is controlled by a security latch mechanism or coupling control device indicated generally at 220 (see FIG. 14). This coupling control device comprises an external slider switch 221, movable in a slider track 2210 on the outside of the body (FIG. 11), in this embodiment circumferentially. Referring again to FIG. 14, the slider switch 221 connects to the body interior through an operating slot and is joined (in this case integrally) with a laterally slidable latch element 222 having an upward detent or abutment edge 223. Connected to the latch element 222 (again, as a one-piece moulding in the present embodiment) are a biasing spring 224, reacting against a spring reaction point 225 formed on the inside of the body shell, and a latch tip extension 229 which, at one extremity of the latch's movement, is caught underneath a latch tip support 226 also formed fixedly on the inside of the body shell 2. By these connections of the latch 222 to the support 226 on one side and the retained slider 221 on the other, the latch element 222 is held firmly and strongly relative to the body just inside the entry opening 227.

Figure 11:
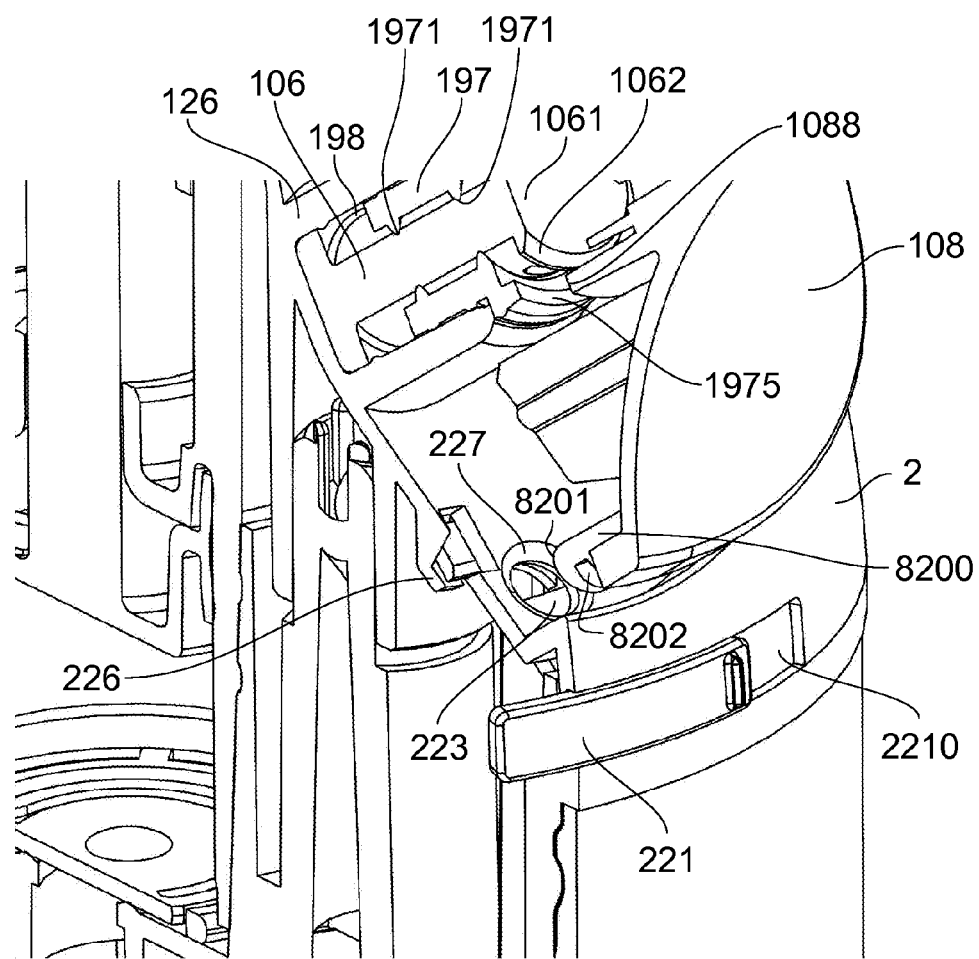
FIGS. 11 to 16 show a third embodiment with an alternative child-resistant coupling control mechanism and also an alternative closure mechanism at the outlet.

The biasing spring 224 is pre-loaded so as normally to urge the latch element 222 and slider 221 to the position seen in FIG. 11, where the abutment edge 223 of the latch blocks the lower part of the entry opening 227. In this condition the nozzle 108 cannot be pushed from its holding position to the coupled position, because the latch element 222 does not give way inwardly. To couple the nozzle, the user must move the slider switch 221 to the right, against the force of the spring 224, to the open position seen in FIGS. 13 and 14. The nozzle 108 is pushed on and its control projection 8200 enters the opening 227. Once it is fully on (and the closure valve thereby opened, see below) the shoulder notch 8202 on the underside of projection 8200 is aligned with the latch element 222. When the slider is released, its abutment edge 223 moves into the notch 8202 and then holds the nozzle 108 securely against being pushed or pulled out of the coupled condition. See FIGS. 15 and 16.

Again, this child-resistant mechanism requires an understanding coordination of the correct movements of the slider switch against its bias and pushing on the nozzle attachment 108, in a condition in which the latch mechanism is otherwise masked by the nozzle surround. To assist adult users when they initially open the dispenser, the latch element 222 may have a contrasting colour to the body so that with the nozzle removed (e.g. by means of removal of the overcap) the user readily observes how this relates to operation of the slider, although a child would not do so.

Figure 12:
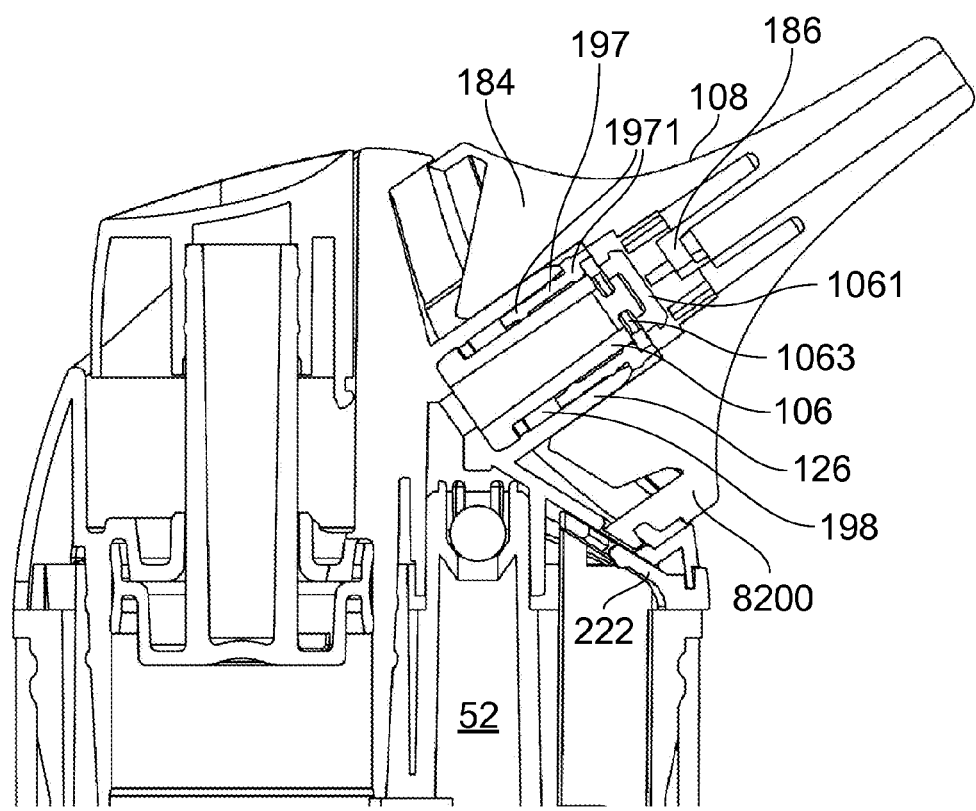
Figure 13:
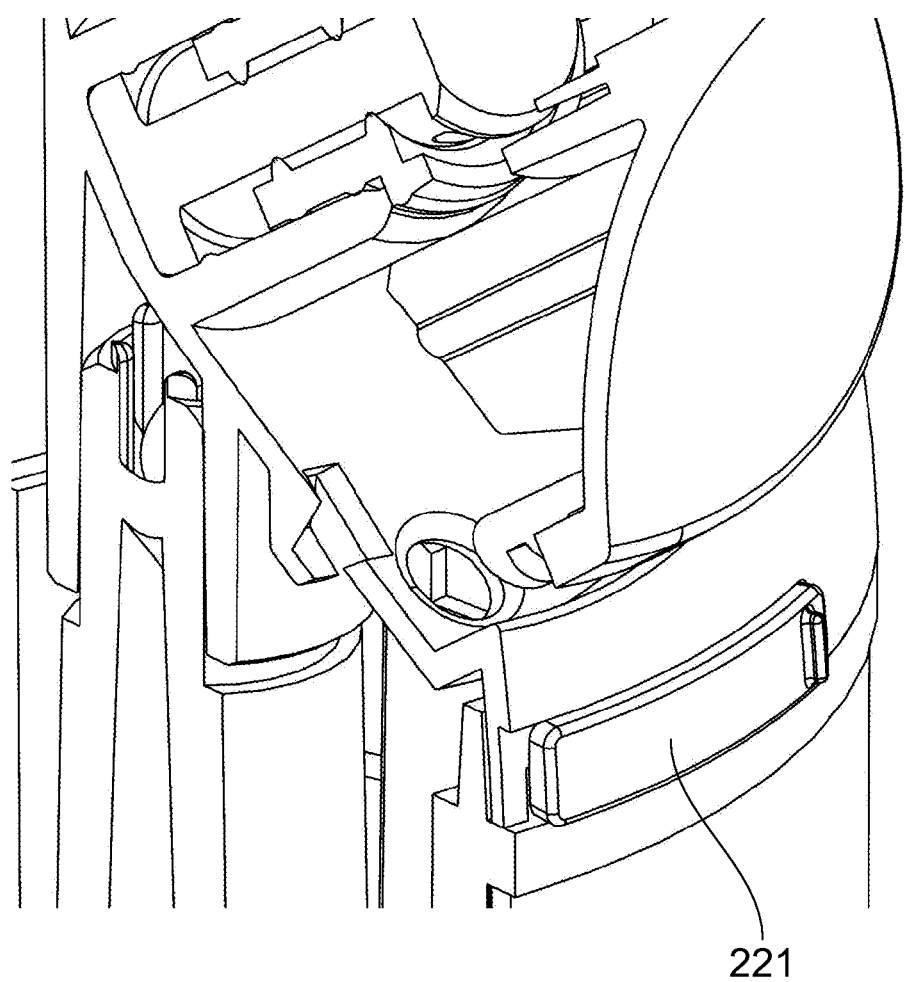
Figure 14:
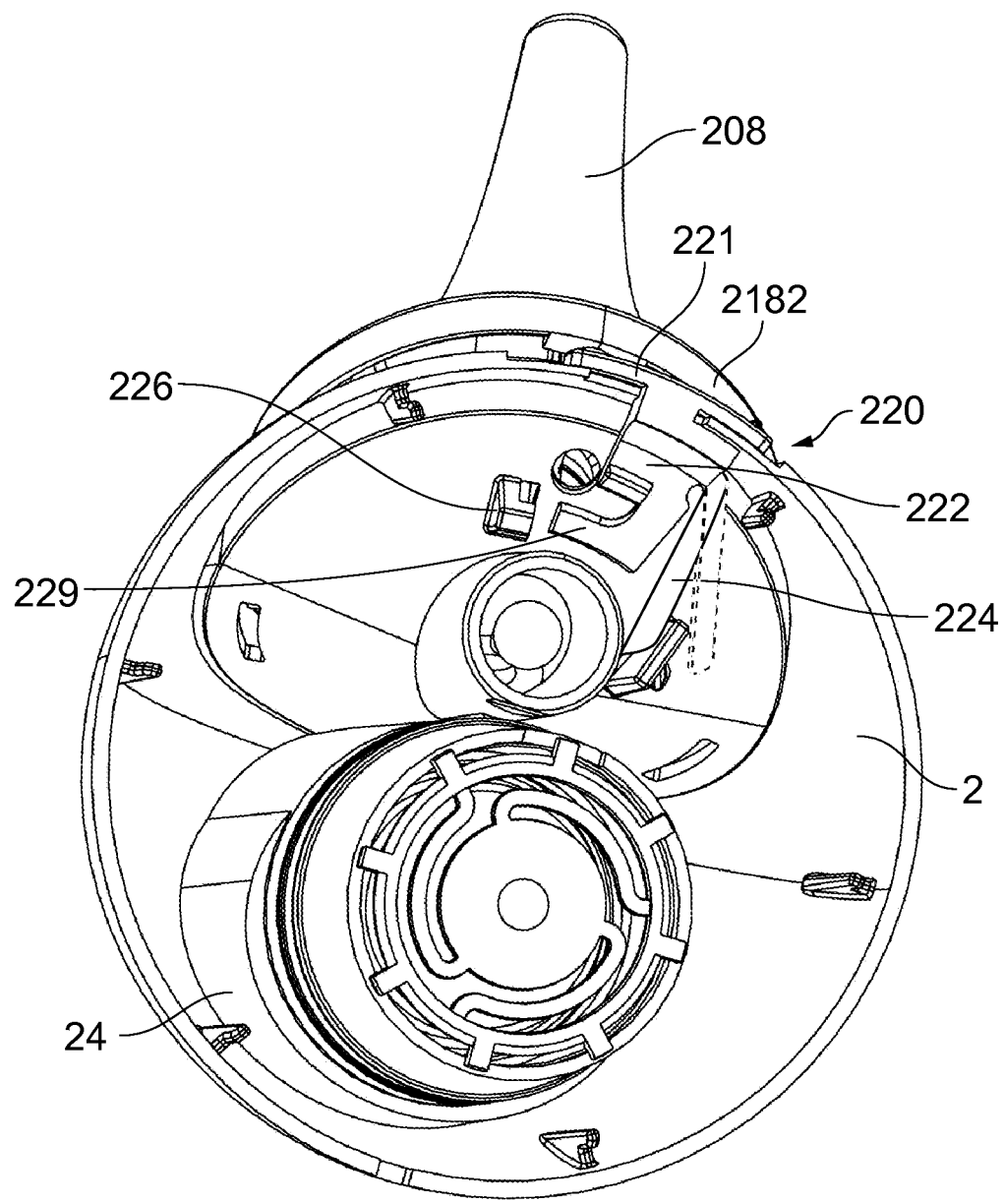
Figure 16:
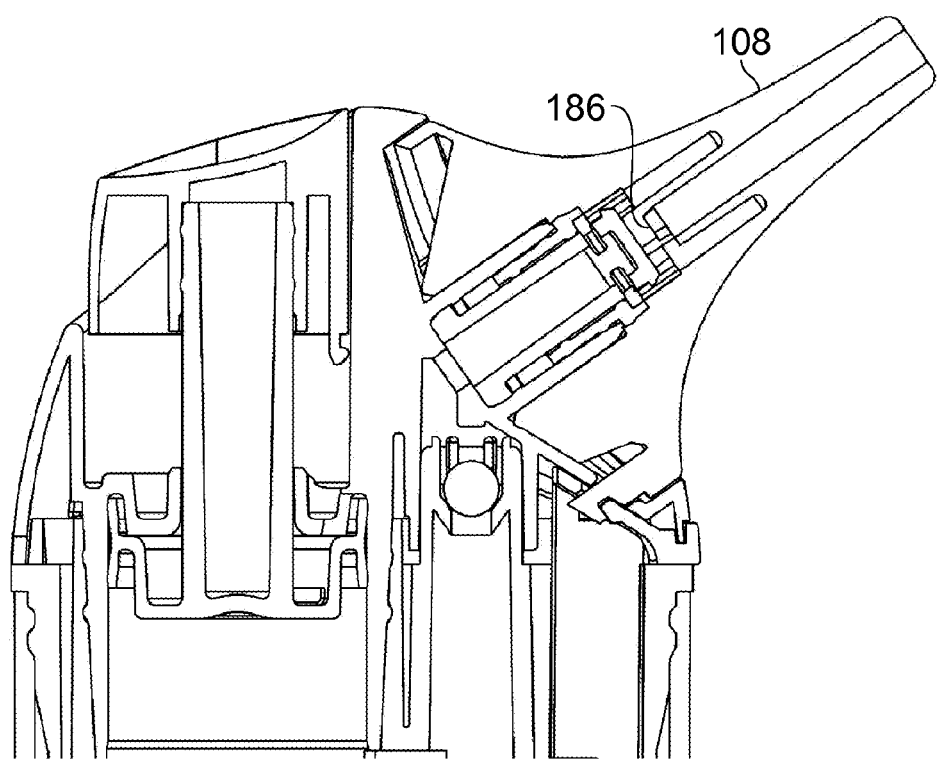

This embodiment also shows an alternative closure valve. The earlier embodiments used an all-plastics one-piece closure valve with integral spring legs. This is effective and hygienic but the spring force is small. It is adequate to operate the valve, but not to push the nozzle back out of the coupled condition, which may be a desired behaviour. The plastic spring legs are also liable to weaken with repeated use. A metal spring, e.g. helical spring gives a much higher force. However with many products e.g. oral products a metal spring cannot be tolerated in contact with the product dispensed and so must be positioned outside the dispensing path. This embodiment provides such a closure valve as seen in FIGS. 11, 12 and 16.

As in the earlier embodiment, a generally cylindrical tubular stub outlet mounting 126 projects integrally from the centre of the mounting nozzle recess. A tubular outlet component 106 with a blind front end wall 1061 is snap-mounted in this, and has laterally (radially) directed outlet openings 1063 near its tip, beneath a projecting annular ledge 1062 of the top wall 1061. In use, a corresponding central stop abutment 186 of the nozzle attachment 108 (see FIGS. 12, 16) meets this front end wall 1061 to limit movement of the nozzle at the centre.

The closure member function is provided by an external sealing or closure sleeve 197. It has first and second spaced interior sealing beads 1971 which fit closely against the cylindrical outer surface of the outlet tube 106. At the top of the sleeve 197 is an outward shoulder with a flat outward face, and an outwardly-projecting peripheral collar around its outer edge at a larger diameter so that in the outermost position of the sleeve 197 (not shown) the underside of the fixed tube wall end ledge 1062 abuts substantially sealingly against the outward shoulder at the top of the sealing sleeve 197. The peripheral collar 1075 thereof extends up around the edge of that peripheral flange or ledge 1062. This collar 1075 is the outermost extremity of the sleeve, and is engageable by a corresponding inwardly-directed shoulder 1088 of the outlet attachment 108 which, in the coupled condition (FIG. 16) pushes the sleeve back down the outlet tube 106 thereby opening the flow openings 163 for product to flow into the nozzle 108. This is against the force of a metal helical spring (not shown) trapped in a spring space 198 (FIG. 11) between the base of the outlet tube and the bottom of the sleeve 197. When the nozzle 108 is removed, or is in the preliminary holding position, the sleeve pushes out and, by means of both the outer sealing bead 1971 and the aforementioned abutting flat faces at the top, prevents the escape of any liquid. Further sealing beads are provided on the outside of the sealing sleeve 197 to prevent leakage into other spaces of the nozzle cavity. This assures reliably accurate dosing. The restricted lateral outlet openings 1063 are also found effective to avoid occasional squirting or jetting from the nozzle 108, which might hit the back of a child's throat and cause choking or rejection.

In this embodiment, with a single peripheral coupling control and a strong central spring, there is a tilting action on the coupled nozzle attachment 108. To resist misalignment or leakage as a result, it is provided with a set of closely fitting support ribs or fins 184. These rigidify its central cylindrical union structures in relation to the external flared surround casing. Their front ends are also shaped to complement closely the base of the body recess to inhibit tilting.

Figure 15:
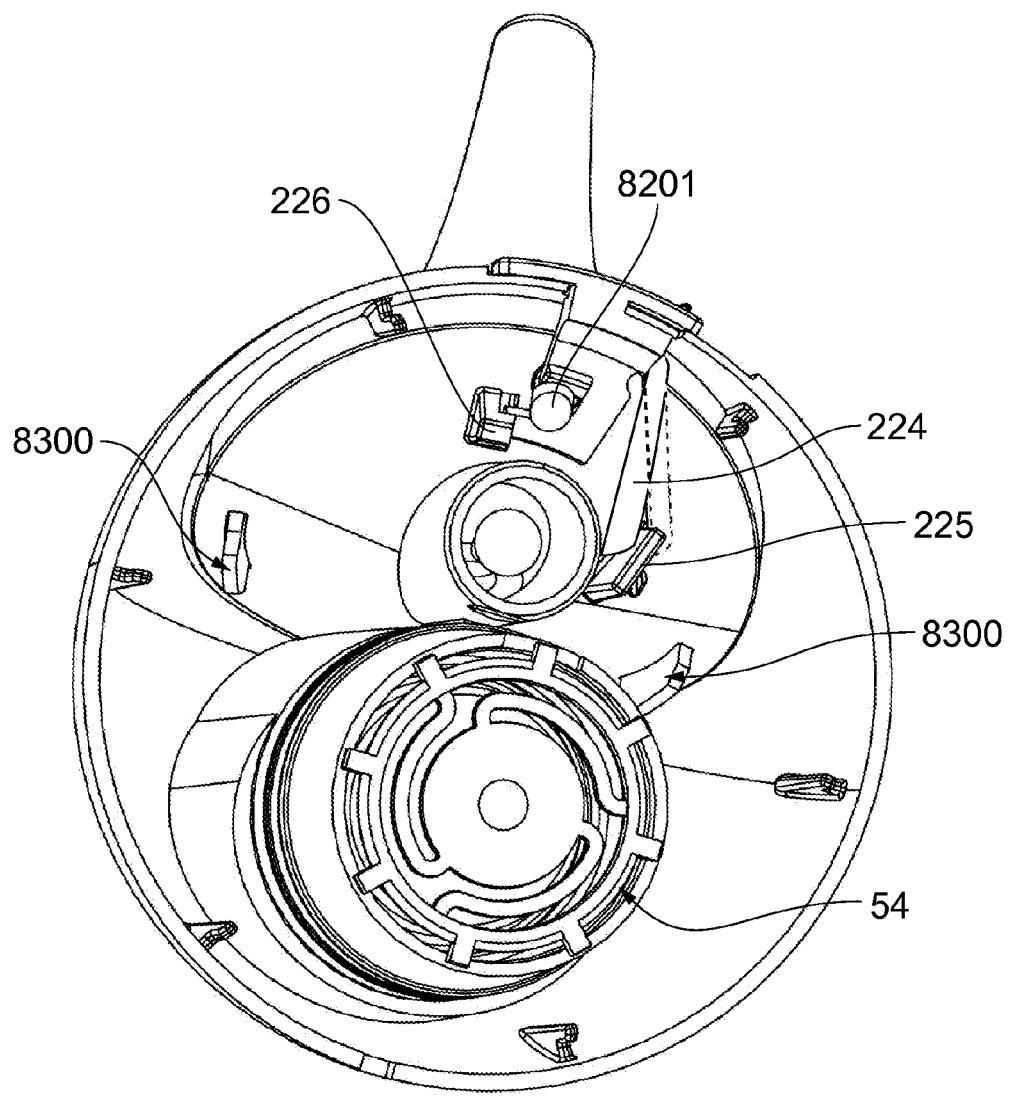
Figure 19:
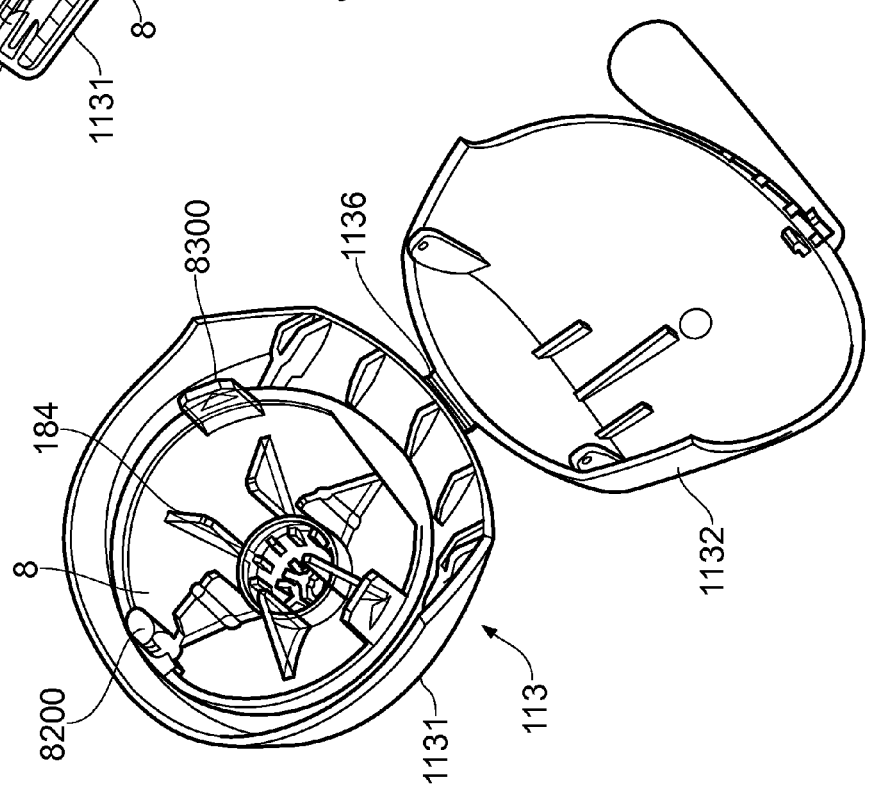

The nozzle attachment again features rearwardly-projecting tabs 8300 (in this case two), which project rearwardly from the inside of the outlet attachment skirt and fit into complementary slots on the dispenser body—see FIG. 15 (and FIG. 19). Although here less critical for the child-resistance per se they must be aligned for the outlet to be pushed on, and assure its correct alignment relative to the body for engagement of the coupling control projection 8200.

Finally, and independently, these embodiments show a distinctive construction of the one-piece valve unit 54. This valve unit comprises a central circular disc flap connected to an outer annulus by plural (e.g. three) flexible legs. The legs have circumferentially-extending intermediate portions to allow for substantial deflection of the disc out of plane. Such a valve is known per se, although more commonly used in removable-nozzle pumps. In the present fixed-nozzle construction the outlet flow (see FIG. 1 and FIG. 5) leaves the pump chamber past the annular edge of the valve unit 54. To facilitate this flow (and so reduce the effort needed to operate the pump) the outer annulus is therefore provided with a series circumferential interruptions, in this case uniform gaps between a series of spaced radial lugs (e.g. 5 to 10 lugs, here 8), which allow the valve unit to be clamped in any orientation between the body and cylinder parts as required, and providing better clearance for outlet flow. This valve construction is an independent feature proposed herein, and may be used in other dispensers, especially fixed-nozzle dispensers.

Figure 20:
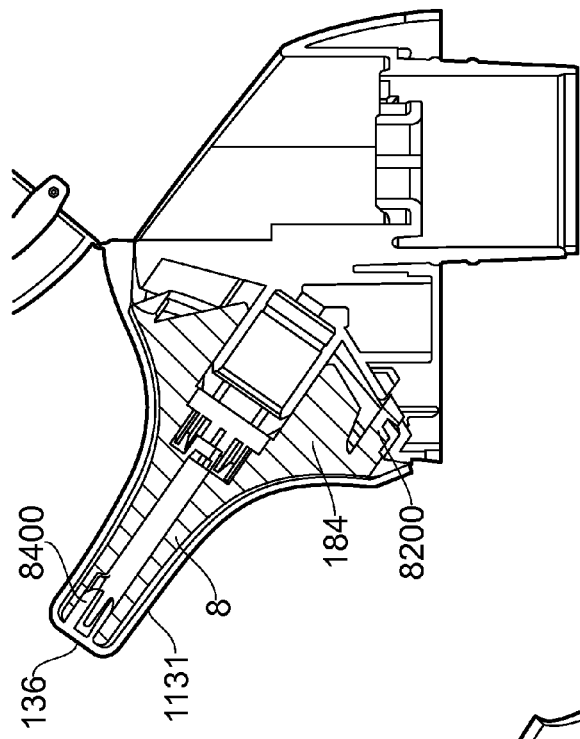
FIGS. 19 to 21 show a fifth embodiment having a special engagement between the overcap and nozzle, the child-resistance structures being as in the third embodiment.
Figure 21:
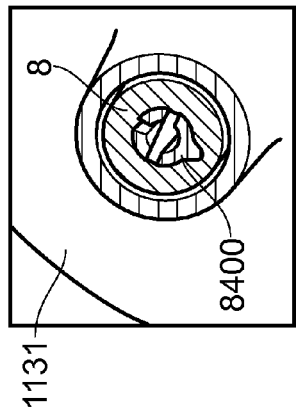

FIGS. 19 to 21 illustrate the option mentioned above in which the protective overcap 113 can hold the nozzle. It includes a projection 8400 which extends in from the tip wall 136 into the nozzle opening 81. This projection may be a single moulded plug and preferably has plural fingers to give resilient outward grip against the interior of the nozzle opening 81. This effectively provides docking of the nozzle attachment in the overcap. The grip strength is sufficient to overcome the provisional (holding) coupling between the nozzle attachment 8 and the stub nozzle 6, so that when the overcap 113 is removed the nozzle attachment 8 comes away with it. The user then pulls it out for fitting onto the dispenser. This avoids possible user confusion, in that a user who did not consult the instructions or look carefully might assume the dispenser to be faulty if it will not operate after removing the cover. Preliminary removal of the nozzle prevents this.

The holding projection 8400 inside the tip wall of the cover may have a non-symmetric cross-section as shown in FIG. 21, to ensure that if the separate nozzle is put in the cover, its circumferential or rotational orientation is correct for fitting.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:
1. A dispenser for fluid product, the dispenser comprising:
  a dispenser body, the dispenser body comprising a discharge outlet defining an outlet opening and an outlet closure valve with a closure mechanism comprising a closure member which in a closed position closes the discharge outlet;
  an outlet attachment, the outlet attachment defining an outlet conduit having a nozzle opening, and which can be coupled to the dispenser by a coupling structure, the coupling structure comprising respective coupling elements of the dispenser body and outlet attachment which interfit, and so that in a coupled condition fluid product can be dispensed from the dispenser through the outlet attachment;
  said coupling structure providing that the coupling of the outlet attachment to the dispenser comprises a completion movement to reach said coupled condition in which fluid product can be dispensed from the dispenser through the outlet attachment; and
  the dispenser comprising additionally a security mechanism, the security mechanism comprising respective cooperating elements of the dispenser body and outlet attachment, and the security mechanism being adjustable between a blocking condition, in which said cooperating elements co-operate to block the completion movement, and an access condition in which said cooperating elements allow the completion movement.

2. The dispenser of claim 1 wherein the cooperating elements of the dispenser body and outlet attachment in the security mechanism comprises an entry path defined by one of said body and attachment,
  a projecting portion of the other of said body and attachment which enters said entry path for said coupling, and
  a movable element positioned adjacent to the entry path and adjustable to prevent movement along the entry path to the coupled condition.

3. The dispenser of claim 2 wherein the security mechanism includes a biasing means which urges the movable element towards the blocking condition.

4. The dispenser of claim 2 wherein the movable element is inside the dispenser body.

5. The dispenser of claim 2 wherein the projecting portion has an abutment surface and the security mechanism comprises a retaining formation which engages with the abutment surface of the projecting portion when in the coupled condition, thereby holding the outlet attachment in the coupled condition.

6. The dispenser of claim 2 in which the security mechanism comprises a movable control member on the dispenser body for said adjustment between the blocking condition and the access condition.

7. The dispenser of claim 6 wherein the control member is a push button, pad, lever or slider on the dispenser body.

8. The dispenser of claim 1 in which the outlet attachment further comprises an actuating structure which in the coupled condition engages the closure mechanism of the outlet closure valve to hold the closure valve in an open condition with the dispenser discharge outlet in fluid communication with the outlet conduit and nozzle opening of the outlet attachment so that fluid product can be dispensed from the dispenser through the outlet attachment, whereas in an uncoupled condition the closure mechanism is operable to move to a closed condition wherein the closure member of its closure valve closes the outlet opening.

9. The dispenser of claim 1 in which the outlet attachment is a one-piece molded plastics nozzle.

10. The dispenser of claim 1 in which the outlet attachment is a tapering nozzle diverging rearwardly to a wider base, and in which in the coupled condition said base covers an entry opening of an entry path.

11. The dispenser of claim 1 in which the dispenser body comprises a projecting nozzle, outlet stub or spigot defining said outlet opening, the outlet attachment fixing onto, over or into said projecting nozzle, outlet stub or spigot in the coupled condition.

12. The dispenser of claim 11 in which the completion movement is a linear slide of the outlet attachment fixing onto, over or into said projecting nozzle, outlet stub or spigot.

13. The dispenser of claim 1 which is a pump dispenser comprising a pump plunger.

14. The dispenser of claim 13 which is a fixed-outlet pump dispenser and comprises a removable protective cover which overlies the top of the plunger and adjacent portions of the dispenser body, to prevent depression of the pump plunger until the cover is removed.

15. The dispenser of claim 14 in which the coupling structure provides a preliminary holding engagement for the outlet attachment in a holding position on or adjacent the dispenser body discharge outlet but not in the coupled condition, and in which the removable protective cover comprises an outlet attachment cover portion conforming to the outside of the outlet attachment in the holding position, and engages with portions of the dispenser body adjacent to the outlet attachment, to prevent said completion movement until the cover is removed.

16. The dispenser of claim 15 wherein the outlet attachment cover portion of the removable protective cover includes gripping means to engage the outlet attachment, thereby retaining the outlet attachment within the protective cover and removing the outlet attachment from the discharge outlet when in the uncoupled condition.

17. The dispenser of claim 14 wherein the removable protective cover comprises a tear-off tab connected to the protective cover by a frangible link and comprising a barbed projection for permanent connection to the dispenser body.

18. The dispenser of claim 13 which is an oral doser for medicine, and the pump dispenser has a pump chamber with a pump chamber volume corresponding to a dosage up to 10 ml.

19. The dispenser of claim 1 wherein the closure member includes a plug portion which is received within said outlet opening in said closed position.

20. A dispenser for fluid product, the dispenser comprising
a dispenser body, the dispenser body comprising a discharge outlet defining an outlet opening and an outlet closure valve with a closure mechanism comprising a closure member which in a closed position closes the discharge outlet;
an outlet attachment, the outlet attachment defining an outlet conduit having a nozzle opening, and which can be coupled to the dispenser by a coupling structure, the coupling structure comprising respective coupling elements of the dispenser body and outlet attachment which interfit, and so that in a coupled condition fluid product can be dispensed from the dispenser through the outlet attachment;
the coupling of the outlet attachment to the dispenser by said coupling structure comprising a completion movement to said coupled condition in which fluid product can be dispensed from the dispenser through the outlet attachment; and
the dispenser being a fixed-outlet pump comprising a pump plunger and a dispenser head housing, comprising additionally a removable protective cover which overlies the top of the plunger and adjacent portions of the dispenser head housing, to prevent or inhibit depression of the plunger until the cover is removed.

21. The dispenser of claim 20 which further includes a security mechanism which is adjustable between a blocking condition and an access condition.

22. The dispenser of claim 21 wherein said security mechanism includes cooperating elements of the dispenser body and outlet attachment.

23. The dispenser of claim 22 wherein the cooperating elements of the dispenser body and outlet attachment in the security mechanism comprise an entry path defined by one of said dispenser body and attachment and a projecting portion of the other of said dispenser body and outlet attachment.

24. The dispenser of claim 23 wherein said security mechanism includes a biasing means for urging a movable element toward said blocking condition.

25. The dispenser of claim 20 wherein the outlet attachment is a one-piece molded plastic nozzle.

26. The dispenser of claim 20 wherein the outlet attachment is a tapering nozzle diverging rearwardly to a wider base, and in which in the coupled condition said base covers an entry opening of an entry path.

27. The dispenser of claim 20 wherein the dispenser body comprises a projecting nozzle, outlet stub or spigot defining said outlet opening, the outlet attachment fixing onto, over or into said projecting nozzle, outlet stub or spigot in the coupled condition.

28. The dispenser of claim 20 wherein the closure member includes a plug portion which is received within said outlet opening in said closed position.

29. A dispenser for a fluid product comprising:
a dispenser body defining an outlet opening;
an outlet closure valve assembled into said outlet opening, said outlet closure valve including a movable closure member;
an outlet attachment assembled to said dispenser body and including an outlet closure valve actuating member and defining a dispensing outlet, said outlet attachment being movable along a path; and
a security mechanism which is constructed and arranged to be adjustable between a blocking condition and an access condition, wherein when said security mechanism is in said blocking condition movement of said outlet attachment along said path is blocked, and wherein when said outlet attachment completes said movement along said path, the outlet closure valve is opened by said outlet closure valve actuating member.

30. The dispenser of claim 29 wherein said outlet closure valve is a normally-closed structure.

31. The dispenser of claim 30 wherein said outlet attachment is separate from said dispenser body prior to attachment.

32. The dispenser of claim 29 which further includes a coupling structure including a first coupling element as part of said dispenser body and a cooperating second coupling element as part of said outlet attachment.

33. The dispenser of claim 29 wherein said security mechanism is spring biased.

34. The dispenser of claim 29 wherein the outlet attachment is a tapering nozzle diverging rearwardly to a wider base.

35. The dispenser of claim 29 wherein the closure member includes a plug portion which is received within said outlet opening when in a closed position.

* * * * *